United States Patent [19]

Morikawa et al.

[11] Patent Number: 5,264,639
[45] Date of Patent: Nov. 23, 1993

[54] PROCESS FOR PRODUCING A 2,2-DIFLUOROPROPANE

[75] Inventors: Shinsuke Morikawa, Yokohama; Shunichi Samejima, Tokyo; Hidekazu Okamoto; Keiichi Ohnishi, both of Yokohama; Shin Tatematsu, Tokyo; Toshihiro Tanuma, Yokohama; Takashi Ohmori, Tokyo, all of Japan

[73] Assignee: Asahi Glass Company Ltd., Tokyo, Japan

[21] Appl. No.: 885,250

[22] Filed: May 20, 1992

Related U.S. Application Data

[63] Continuation of Ser. No. 582,197, Oct. 2, 1990, abandoned.

[30] Foreign Application Priority Data

| Feb. 2, 1989 | [JP] | Japan | 1-22550 |
| Feb. 2, 1989 | [JP] | Japan | 1-22621 |
| Feb. 3, 1989 | [JP] | Japan | 1-23741 |
| Feb. 3, 1989 | [JP] | Japan | 1-23742 |
| Feb. 3, 1989 | [JP] | Japan | 1-23743 |
| Feb. 3, 1989 | [JP] | Japan | 1-23744 |
| Feb. 3, 1989 | [JP] | Japan | 1-23745 |
| Feb. 3, 1989 | [JP] | Japan | 1-23750 |
| Feb. 6, 1989 | [JP] | Japan | 1-25653 |
| Feb. 6, 1989 | [JP] | Japan | 1-25654 |
| Feb. 6, 1989 | [JP] | Japan | 1-25655 |
| Feb. 6, 1989 | [JP] | Japan | 1-25656 |
| Feb. 6, 1989 | [JP] | Japan | 1-25657 |
| Feb. 6, 1989 | [JP] | Japan | 1-25658 |
| Feb. 6, 1989 | [JP] | Japan | 1-25681 |

[51] Int. Cl.⁵ .............. C07C 17/00; C07C 17/08
[52] U.S. Cl. .............. 570/168; 570/166; 570/169; 570/167
[58] Field of Search .......... 570/167, 166, 168, 169

[56] References Cited

U.S. PATENT DOCUMENTS 2,005,707  6/1935  Daudt et al. ............... 570/167
2,490,764  12/1949  Benning et al. .
2,578,721  12/1951  McBee et al. .

FOREIGN PATENT DOCUMENTS 0317981  5/1989  European Pat. Off. .
938070   9/1963  United Kingdom .
945017   12/1963 United Kingdom .
975498   11/1964 United Kingdom .
999444   7/1965  United Kingdom .

OTHER PUBLICATIONS

Houben-Weyl: Methoden der Organischen Chemie, 4th Edition, vol. V/3, "Halogenverbindungen", 1962, Georg Thieme Verlag, pp. 124-125.

*Primary Examiner*—Alan Siegel
*Attorney, Agent, or Firm*—Oblon, Spivak, McClelland, Maier & Neustadt

[57] ABSTRACT

A process for producing a 2,2-difluoropropane of the following formula (2), which comprises fluorinating a chlorine-containing 2,2-halogenopropane of the following formula (1) by hydrogen fluoride or a fluorinating agent:

$$C_3H_aCl_bF_c \qquad (1)$$

$$C_3H_aCl_{b-x}F_{c+x} \qquad (2)$$

wherein a, b, c and x are integers satisfying the following conditions:

$$a \geq 0, \ b \geq 1, \ c \geq 0, \ x \geq 1, \ a+b+c=8.$$

6 Claims, No Drawings

PROCESS FOR PRODUCING A 2,2-DIFLUOROPROPANE

This application is a continuation of application Ser. No. 07/582,197, filed on Oct. 1, 1990, now abandoned.

TECHNICAL FIELD

The present invention relates to a process for producing a 2,2-difluoropropane.

BACKGROUND TECHNIQUE

As a synthetic route for a 2,2-difluoropropane, a method has been known which comprises adding dichlorodifluoromethane or trichlorofluoromethane to an ethylene having a difluoromethylene unit, such as 1,1-dichloro-2,2-difluoroethylene or 1-chloro-1,2,2-trifluoroethylene, in the presence of aluminum chloride.

However, such a method has a drawback that it produces not only the desired product but also a reaction by-product having a methylene group other than the 2,2-difluoromethylene and having a boiling point close to that of the desired product, whereby a multi stage purification process is required in order to obtain a product of a high purity. Further, a method for synthesizing 1-chloro-1,1,2,2-tetrafluoropropane is known which comprises fluorinating propyne ($CH_3C\equiv CH$) with hydrogen fluoride to obtain 2,2-difluoropropane ($CH_3CF_2CH_3$), then selectively chlorinating only three hydrogen atoms at 1-position with chlorine to obtain 1,1,1-trichloro-2,2-difluoropropane ($CCl_3CF_2CH_3$), and further selectively fluorinating only two out of the three chlorine atoms substituted on the carbon atom at the 1-position to obtain 1-chloro-1,1,2,2-tetrafluoropropane (J. Am. Chem. Soc., 65, 2342 (1943)). This method requires many steps and thus has a drawback that it is difficult to improve the yield, and the method is not suitable for industrial production. Further, a method for preparing 1-chloro-2,2,3,3-tetrafluoropropane is known which comprises producing 2,2,3,3-tetrafluoropropanol from tetrafluoroethylene and methanol, then reacting it with sulfuryl chloride to obtain a chlorosulfonic acid ester, and then reacting it with an alkali metal chloride. This method requires many steps, whereby it is difficult to improve the yield, and thus has a drawback that such a method is not suitable for industrial production.

Further, a method for preparing 1-chloro-2,2,3-trifluoropropane is known which comprises dehydrochlorinating 1,2,3-trichloropropane to obtain 2,3-dichloropropene, reacting it with potassium fluoride to obtain 2-chloro-3-fluoropropene, then adding chlorine thereto to obtain 1,2,2-trichloro-3-fluoropropane, and then fluorinating it with antimony dichloride trifluoride. Such a method requires many steps. Therefore, the method has a drawback that it is difficult to improve the yield. As such, the method is not suitable for industrial production.

DISCLOSURE OF THE INVENTION

The present inventors have conducted extensive researches for a process of effectively producing a 2,2-difluoropropane and, as a result, they have found it possible to obtain a 2,2-difluoropropane of the following formula (2) in good yield by fluorinating a chlorine-containing 2,2-halogenopropane of the formula (1) with hydrogen fluoride or a fluorinating agent. The present invention is based on this discovery.

The present invention provides a process for producing a 2,2-difluoropropane of the following formula (2), which comprises fluorinating a chlorine-containing 2,2-halogenopropane of the following formula (1) by hydrogen fluoride or a fluorinating agent:

$$C_3H_aCl_bF_c \qquad (1)$$

$$C_3H_aCl_{b-x}F_{c+x} \qquad (2)$$

wherein a, b, c and x are integers satisfying the following conditions:

$$a \geq 0,\ b \geq 1,\ c \geq 0,\ x \geq 1,\ a+b+c = 8.$$

The 2,2-difluoropropane is useful as an etching agent for the production of electronic parts. Further, a chlorine-containing 2,2-difluoropropane is expected to be useful as a foaming agent, a cooling medium, a propellant or a solvent like conventional chlorofluorocarbons. Particularly, it is expected to be useful as a solvent which can be a substitute for 1,1,2-trichlorotrifluoroethane. Further, it hardly depletes the ozone layer in the stratosphere. It is also useful as an intermediate for the production of a hydrogen-2,2-difluoropropane containing no chlorine.

BEST MODE OF CARRYING OUT THE INVENTION

Now, the present invention will be described in detail with reference to the preferred embodiments.

The fluorination in the present invention is preferably conducted by hydrogen fluoride in the presence of a fluorination catalyst, or by a fluorinating agent.

As the fluorination catalyst, a halide of niobium, tantalum or antimony, such as niobium fluoride, niobium chloride, tantalum pentafluoride, tantalum pentachloride, antimony pentafluoride, antimony pentachloride, antimony trifluorodichloride or antimony trifluorodibromide, may be used. When such a fluorination catalyst is employed, the fluorination reaction may be conducted in a gas phase, but is preferably conducted in a liquid phase under atmospheric pressure or under pressurization at a temperature within a range of from 0° to 200° C., preferably from room temperature to 150° C.

The reaction is conducted usually in the absence of a solvent. However, a solvent may be employed. In such a case, there is no particular restriction as to the solvent, so long as it is capable of dissolving the propane as the starting material and it is hardly fluorinated as compared with the starting material. The pressure for the reaction is not particularly limited, but it is usually within a range of from 0 to 30 kg/cm². If a solvent is used, the pressure may vary depending upon the type of the solvent.

Hydrogen fluoride may be charged together with the propane as the starting material to the reactor prior to the reaction. However, it is preferred to introduce it into the liquid phase at the time of the reaction.

The ratio between hydrogen fluoride and the chlorine-containing 2,2-halogenopropane starting material may be varied in a wide range. However, in order to substitute the chlorine atoms, it usually uses stoichiometrical amount of hydrogen fluoride. It is however possible to use hydrogen fluoride in an amount substantially larger than the stoichiometrical amount (for example, 4 mol times or higher, relative to the total molar amount of the starting material.

The contact time is usually from 10 seconds to 10 hours, preferably from 30 seconds to 1 hour.

As other catalysts, fluorination catalysts composed of halides or oxides containing at least one element selected from the group consisting of Al, Cr, Mg, Ca, Ba, Sr, Fe, Ni, Co and Mn, may be used. To prepare such catalysts, any method may be employed so long as it is capable of uniformly dispersing the halides or oxides containing at least one element selected from the group consisting of the above ten elements. For example, a coprecipitation method or a kneading method may be mentioned. Particularly preferred is a method in which hydrates are co-precipitated from an aqueous solution of salts of the above metal elements, or a method wherein a cake of hydroxides is kneaded and pulverized by a ball mill or by a homogenizer. The hydroxides may be those precipitated from aqueous solutions of inorganic salts such as nitrates or sulfates by means of aqueous ammonia or urea, or those prepared by the hydrolysis of organic salts.

A catalyst in the state of a hydrate is preferably dried at a temperature of from 129° to 150° C., followed by calcining at a temperature of from 300° to 600° C., preferably from 350° to 450° C.

It is preferred to activate the catalyst. Such activation can be accomplished usually by applying fluorinating treatment at a temperature of from 100° to 450° C., preferably from 200° to 350° C. Otherwise, such activation can be conducted in the fluorination reaction system, or by heat treatment together with a fluorinated hydrocarbon.

When the above catalyst is used, the fluorination reaction may be conducted in a liquid phase. However, it is preferred to conduct the fluorination reaction in a gas phase under atmospheric pressure or under pressurization at a temperature within a range of from 150° to 550° C., more preferably from 250° to 450° C.

The ratio between hydrogen fluoride and the chlorine-containing 2,2-halogenopropane starting material, may be varied in a wide range. However, in order to substitute the chlorine atoms, it usually uses stoichiometrical amount of hydrogen fluoride. However, hydrogen fluoride may be used in an amount substantially larger than the stoichiometrical amount, for example, 4 mol times or more, relative to the total molar amount of the starting material. The contact time is usually from 0.1 to 300 seconds, preferably from 5 to 30 seconds.

To maintain the catalytic activity, oxygen or chlorine is preferably added in an amount of from 0.1 to 10% by volume relative to the chlorine-containing 2,2-halogenopropane starting material.

When the fluorination reaction is conducted with a fluorinating agent, a fluorinating agent composed of a fluoride, fluorohalide or oxyfluoride containing at least one element selected from the group consisting of Mn, Ag, Sb, Ta, Nb, Ce, Co, Al, Cr, Mg, Ca, Ba, Zn, Si, Li, Na, K, Cs and Rb, may be used. The reaction can be conducted in a gas phase or in a liquid phase. Specifically, $MnF_3$, $AgF$, $AgF_2$, $SbF_3$, $SbF_3Cl_2$, $SbF_5$, $TaF_5$, $NbF_5$, $CeF_4$, $CoF_3$, $AlClF_2$, $CrO_2F_2$, $LiF$, $NaF$, $KF$, $CsF$, $RbF$, $KF\text{-}MgF_2$, $KF\text{-}CaF_2$, $KF\text{-}BaF_2$, $ZnF_2$, $SiF_2$ and $NaSiF_6$, may be mentioned.

There is no particular restriction as to the amount of fluorinating agent to be used for the fluorination reaction. It is preferred to use a stoichiometric amount of the fluorinating agent relative to the number of chlorine atoms to be substituted in the starting material. However, in order to substantially completely react all the chlorine atoms to be substituted, the fluorinating agent may be used in an amount substantially larger than the stoichiometrical amount, for example, 2 mol times or more, relative to the number of chlorine atoms to be substituted in the starting material. After the reaction, the fluorinating agent is recovered in the form of a chloride or oxychloride, and may be regenerated by means of hydrogen fluoride or fluorine gas. The conditions for the fluorination reaction vary depending upon the fluorinating agent to be employed. However, the reaction temperature is usually from 0° to 450° C., preferably from 50° to 300° C. The reaction time is usually from 1 minute to 20 hours, preferably from 1 to 10 hours. The reaction may be conducted in the absence of a solvent. However, depending upon the fluorinating agent, it is preferred to employ a solvent. As a solvent to be used for the reaction, benzene, toluene, benzotrifluoride, a glycol such as ethylene glycol, or an aprotic polar solvent such as N,N-dimethylformamide, N,N-dimethylacetamide, dimethylsulfoxide, dimethylsulfone, sulforane, hexamethylphosphotriamide, N-methyl-2-pyrrolidone, acetonitrile, benzonitrile, nitromethane, dioxane, diglime, tetraglime or acetone, may be mentioned. Particularly when an alkali metal fluoride such as KF or CsF is used as the fluorinating agent, sulforane or N,N-dimethylformamide is preferred. A phase transfer catalyst may be added as a reaction accelerating agent. As such a phase transfer catalyst, a quaternary ammonium salt such as tetramethyl ammonium chloride or tetrabutyl ammonium bromide, or a quaternary phosphonium salt such as tetrabutylphosphonium bromide or tetraphenylphosphonium bromide, or crown ether may be mentioned. Such a phase transfer catalyst is added usually in an amount of from 0.01 to 100% by weight, preferably from 0.1 to 30% by weight, relative to the alkali metal fluoride. When $SbF_3$, $SbF_3Cl_2$ or $SbF_5$ is used as the fluorinating agent, $SbCl_3$ or $SbCl_5$ may be added as a catalyst. $SbCl_3$ or $SbCl_5$ may be added usually in an amount of 0.01 to 100% by weight, preferably from 0.1 to 20% by weight, relative to $SbF_3$, $SbF_3Cl_2$ or $SbF_5$.

The following reactions (3) to (7) may be mentioned as specific embodiments for producing a 2,2-difluoropropane of the formula (2) by fluorinating a chlorine-containing 2,2-halogenopropane of the formula (1).

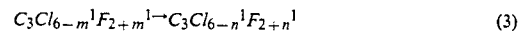

$$C_3Cl_{6-m^1}F_{2+m^1} \rightarrow C_3Cl_{6-n^1}F_{2+n^1} \qquad (3)$$

$$0 \leq m^1 \leq 5 \quad 1 \leq n^1 \leq 6, \quad m^1 < n^1$$

The chlorine-containing 2,2-halogenopropane ($C_3Cl_{6-m^1}F_{2+m^1}$ wherein $0 \leq m^1 \leq 5$) to be used as the starting material includes 1,1,1,3,3,3-hexachloro-2,2-difluoropropane (R-212ca), 1,1,1,3,3-pentachloro-2,2,3-trifluoropropane (R-213ca), 1,1,3,3-tetrachloro-1,2,2,3-tetrafluoropropane (R-214ca), 1,1,1,3-tetrachloro-2,2,3,3-tetrafluoropropane (R-214cb), 1,1,3-trichloro-1,2,2,3,3-pentafluoropropane (R-215ca), 1,1,1-trichloro-2,2,3,3,3-pentafluoropropane (R-215cb), 1,3-dichloro-1,1,2,2,3,3-hexafluoropropane (R-216ca), 1,1-dichloro-1,2,2,3,3,3-hexafluoropropane (R-216cb) and 1-chloro-1,1,2,2,3,3,3-heptafluoropropane (R-217ca).

The 2,2-difluoropropane ($C_3Cl_{6-n^1}F_{2+n^1}$) wherein $1 \leq n^1 \leq 6$) to be formed by the reaction includes 1,1,1,3,3-pentachloro-2,2,3-trifluoropropane (R-213ca), 1,1,3,3-tetrachloro-1,2,2,3-tetrafluoropropane (R-214ca), 1,1,1,3-tetrachloro-2,2,3,3-tetrafluoropropane (R-214cb), 1,1,3-trichloro-1,2,2,3,3-pentafluoropropane (R-215ca), 1,1,1-trichloro-2,2,3,3,3-pentafluoro-propane (R-215cb), 1,3-dichloro-1,1,2,2,3,3-hexafluoropropane (R-216ca), 1,1-dichloro-1,2,2,3,3,3-hexafluoropropane (R-216cb), 1-chloro-1,1,2,2,3,3,3-heptafluoropropane (R-217ca) and octafluoropropane (R-218). These products can be separated by a usual method such as distillation.

$$C_3HCl_{5-m^2}F_{2+m^2} \rightarrow C_3HCl_{5-n^2}F_{2+n^2} \qquad (4)$$

$$0 \leq m^2 \leq 4 \quad 1 \leq n^2 \leq 5, \quad m^2 < n^2$$

The chlorine-containing 2,2-halogenopropane ($C_3HCl_{5-m^2}$ wherein $0 \leq m^2 \leq 4$) to be used as the starting material includes 1,1,1,3,3-pentachloro-2,2-difluoropropane (R-222ca), 1,1,3,3-tetrachloro-1,2,2-trifluoropropane (R-223ca), 1,1,1,3-tetrachloro-2,2,3-trifluoropropane (R-223cb), 1,1,3-trichloro-2,2,3,3-tetrafluoropropane (R-224ca), 1,1,3-trichloro-1,2,2,3-tetrafluoropropane (R-224cb), 1,1,1-trichloro-2,2,3,3-tetrafluoropropane (R-224cc), 1,1-dichloro-2,2,3,3,3-pentafluoropropane (R-225ca), 1,3-dichloro-1,1,2,2,3-pentafluoropropane (R-225cb), 1,1-dichloro-1,2,2,3,3-pentafluoropropane (R-225cc), 1-chloro-1,2,2,3,3,3-hexafluoropropane (R-226ca) and 1-chloro-1,1,2,2,3,3-hexafluoropropane (R-226cb). The 2,2-difluoropropane ($C_3HCl_{5-n^2}F_{2+n^2}$ wherein $1 \leq n^2 \leq 5$) to be formed by the reaction includes 1,1,3,3-tetrachloro-1,2,2-trifluoropropane (R-223ca), 1,1,1,3-tetrachloro-2,2,3-trifluoropropane (R-223cb), 1,1,3-trichloro-2,2,3,3-tetrafluoropropane (R-224ca), 1,1,3-trichloro-1,2,2,3-tetrafluoropropane (R-224cc), 1,1-dichloro-2,2,3,3,3-pentafluoropropane (R-225ca), 1,3-dichloro-1,1,2,2,3-pentafluoropropane (R-225cb), 1,1-dichloro-1,2,2,3,3-pentafluoropropane (R-225cc), 1-chloro-1,2,2,3,3,3-hexafluoropropane (R-226ca), 1-chloro-1,1,2,2,3,3-hexafluoropropane (R-226cb) and 1,1,1,2,2,3,3,-heptafluoropropane (R-227ca). These products can be separated by a usual method such as distillation.

$$C_3H_2Cl_{4-m^3}F_{2+m^3} \rightarrow C_3H_2Cl_{4-n^3}F_{2+n^3} \qquad (5)$$

$$0 \leq m^3 \leq 3 \quad 1 \leq n^3 \leq 4, \quad m^3 < n^3$$

The chlorine-containing 2,2-halogenopropane ($C_3H_2Cl_{4-m^3}F_{2+m^3}$ wherein $0 \leq m^3 \leq 3$) to be used as the starting material includes 1,1,1,3-tetrachloro-2,2-difluoropropane (R-232cb), 1,1,3,3-tetrachloro-2,2-difluoropropane (R-232ca), 1,1,3-trichloro-1,2,2-trifluoropropane (R-233cb), 1,1-dichloro-1,2,2,3-tetrafluoropropane (R-234cd), 1,3-dichloro-1,1,2,2-tetrafluoropropane (R-234cc), 1,1-dichloro-2,2,3,3-tetrafluoropropane (R-234cb), 1,3-dichloro-1,2,2,3-tetrafluoropropane (R-234ca), 1-chloro-1,1,2,2,3-pentafluoropropane (R-235cc), 3-chloro-1,1,1,2,2-pentafluoropropane (R-235cb) and 1-chloro-1,2,2,3,3-pentafluoropropane (R-235ca).

The 2,2-difluoropropane ($C_3H_2Cl_{4-n^3}F_{2+n^3}$ wherein $1 \leq n^3 \leq 4$) to be formed by the reaction includes 1,1,1-trichloro-2,2,3-trifluoropropane (R-233cc), 1,1,3-trichloro-1,2,2-trifluoropropane (R-233cb), 1,1,3-trichloro-2,2,3-trifluoropropane (R-233ca), 1,1-dichloro-1,2,2,3-tetrafluoropropane (R-234cd), 1,3-dichloro-2,2,3,3-tetrafluoropropane (R-234cb), 1,3-dichloro-1,2,2,3-tetrafluoropropane (R-234ca), 1-chloro-1,1,2,2,3-pentafluoropropane (R-235cc), 3-chloro-1,1,1,2,2-pentafluoropropane (R-235cb), 1-chloro-1,2,2,3,3-pentafluoropropane (R-235ca), 1,1,1,2,2,3-hexafluoropropane (R-236cb) and 1,1,2,2,3,3-hexafluoropropane (R-236ca). These products can be separated by a usual method such as distillation.

$$C_3H_3Cl_{3-m^4}F_{2+m^4} \rightarrow C_3H_3Cl_{3-n^4}F_{2+n^4} \qquad (6)$$

$$0 \leq m^4 \leq 2 \quad 1 \leq n^4 \leq 3, \quad m^4 < n^4$$

The chlorine-containing 2,2 halogenopropane ($C_3H_3Cl_{3-m^4}F_{2+m^4}$ wherein $0 \leq m^4 \leq 2$) to be used as the starting material includes 1,1,3-trichloro-2,2-difluoropropane (R-242ca), 1,1,1-trichloro-2,2-difluoropropane (R-242cb), 1,3-dichloro-1,2,2-trifluoropropane (R-243ca), 1,1-dichloro-2,2,3-trifluoropropane (R-243cb), 1,1-dichloro-1,2,2-tetrafluoropropane (R-244ca), 1-chloro-1,2,2,3-tetrafluoropropane (R-244cb) and 1-chloro-1,1,2,2-tetrafluoropropane (R-244cc).

The 2,2-difluoropropane and trihydrochlorofluoropropane ($C_3H_3Cl_{3-n^4}F_{2+n^4}$ wherein $1 \leq n^4 \leq 3$) to be formed by the-reaction include 1,3-dichloro-1,2,2-trifluoropropane (R-243ca), 1,1-dichloro-2,2,3-trifluoropropane (R-243cb), 1,1-dichloro-1,2,2-tetrafluoropropane (R-244ca), 1-chloro-1,2,2,3-tetrafluoropropane (R-244cb), 1-chloro-1,1,2,2-tetrafluoropropane (R-244cc), 1,1,2,2,3-pentafluoropropane (R-245ca) and 1,1,1,2,2-pentafluoropropane (R-245cb). These products can be separated by a usual method such as distillation.

$$C_3H_4Cl_{2-m^5}F_{2+m^5} \rightarrow C_3H_4Cl_{2-n^5}F_{2+n^5} \qquad (7)$$

$$0 \leq m^5 \leq 1 \quad 1 \leq n^5 \leq 2, \quad m^5 < n^5$$

The chlorine-containing 2,2-halogenopropane ($C_3H_4Cl_{2-m^5}F_{2+m^5}$ wherein $0m^5 \leq 1$) to be used as the starting material includes 1,3-dichloro-2,2-difluoropropane (R-252ca), 1,1-dichloro-2,2-difluoropropane (R-252cb), 1-chloro-2,2,3-trifluoropropane (R-253ca) and 1-chloro-1,2,2-trifluoropropane (R-253cb).

The 2,2-difluoropropane ($C_3H_4Cl_{2-n^5}F_{2+n^5}$ wherein $1 \leq n^5 \leq 2$) to be formed by the reaction includes 1-chloro-2,2,3-trifluoropropane (R-253ca), 1-chloro-1,2,2-trifluoropropane (R-253cb), 1,2,2,3-tetrafluoropropane (R-254ca) and 1,1,2,2-tetrafluoropropane (R-254cb). These products can be separated by a usual method such as distillation.

On the other hand, when liquid phase fluorinations taking a long period of time are taken into account, the following reactions (8) to (12) may be mentioned.

$$C_3Cl_{8-m^6}F_{m^6} \rightarrow C_3Cl_{8-n^6}F_{n^6} \qquad (8)$$

$$0 \leq m^6 \leq 5 \quad 2 \leq n^6 \leq 8, \quad m^6 < n^6$$

The chlorine-containing 2,2-halogenopropane ($C_3Cl_{8-m^6}F_{m^6}$ wherein $0 \leq m^6 \leq 5$) to be used as the starting material includes 1,1,1,2,2,3,3,3-octachloropropane (R-210aa), 1,1,1,2,3,3,3-heptachloro-2-fluoropropane (R-211ba), 1,1,1,3,3,3-hexachloro-2,2-difluoropropane (R-212ca), 1,1,1,3,3-pentachloro 2,2,3-trifluoropropane (R-213ca), 1,1,1,3,3-tetrachloro-1,2,2,3-tetrafluoropropane (R-214ca), 1,1,1,3-tetrachloro-2,2,3,3-tetrafluoropropane (R-214cb), 1,1,1,3-tetrachloro-2,2,3,3-pentafluoropropane (R-215ca) and 1,1,1-trichloro-2,2,3,3,3-pentafluoropropane (R-215cb).

The 2,2-difluoropropane ($C_3Cl_{8-n^6}F_{n^6}$ wherein $2 \leq n^6 \leq 8$ and $m^6 < n^6$) to be formed by the reaction includes 1,1,3,3-tetrachloro-1,2,2,3-tetrafluoropropane (R-214ca), 1,1,1,3-tetrachloro-2,2,3,3-tetrafluoropropane (R-214cb), 1,1,3-trichloro-1,2,2,3,3-pentafluoropropane (R-215ca), 1,1,1-trichloro-2,2,3,3,3-pentafluoropropane (R-215cb), 1,3-dichloro-1,1,2,2,3,3-hexafluoropropane (R-216ca), 1,1-dichloro-1,2,2,3,3,3-hexafluoropropane (R-216cb), 1-chloro-1,1,2,2,3,3,3-heptafluoropropane (R-217ca) and octafluoropropane (R-218ca). These products can be separated by a usual method such as fractional distillation.

$$C_3HCl_{7-m}{}^7F_m{}^7 \rightarrow C_3HCl_{7-n}{}^7F_n{}^7 \qquad (9)$$

$$0 \leq m^7 \leq 4 \; 2 \leq n^7 \leq 7, \; m^7 < n^7$$

The chlorine-containing 2,2-halogenopropane ($C_3HCl_{7-m}{}^7Fm^7$ wherein $0 \leq m^7 \leq 4$) to be used as the starting material includes 1,1,1,2,2,3,3-heptachloropropane (R-220aa), 1,1,1,2,3,3-hexachloro-2-fluoropropane (R-221ba), 1,1,1,3,3-pentachloro-2,2-difluoropropane (R-222ca), 1,1,3,3-tetrachloro-1,2,2-trifluoropropane (R-223ca), 1,1,1,3-tetrachloro-2,2,3-trifluoropropane (R-2123cb), 1,3,3-trichloro-1,1,2,2-tetrafluoropropane (R-224ca), 1,1,3-trichloro-1,2,2,3-tetrafluoropropane (R-2224cb) and 1,1,1-trichloro-2,2,3,3-tetrafluoropropane (R-224cc).

The 2,2-difluoropropane ($C_3HCl_{7-n}{}^7F_n{}^7$ wherein $2 \leq n^7 \leq 7$) to be formed by the reaction includes
1,1,3,3-tetrachloro-1,2,2-trifluoropropane (R-223ca),
1,1,1,3-tetrachloro-2,2,3-trifluoropropane (R-223cb),
1,3,3-trichloro-1,1,2,2-tetrafluoropropane (R-224ca),
1,1,3-trichloro-1,2,2,3-tetrafluoropropane (R-224cb),
1,1,1-trichloro-2,2,3,3-tetrafluoropropane (R-224cc),
3,3-dichloro-1,1,1,2,2-pentafluoropropane (R-225ca),
1,3-dichloro-1,1,2,2,3-pentafluoropropane (R-225cb),
1,1-dichloro-1,2,2,3,3-pentafluoropropane (R-225cc),
3-chloro-1,1,1,2,2,3-hexafluoroproane (R-226ca), 1-chloro-1,1,2,2,3,3-hexafluoropropane (R-226cb) and 1,1,1,2,2,3,3-heptafluoropropane (R-227ca). These products can be separated by a usual method such as fractional distillation.

$$C_3H_2Cl_{6-m}{}^8F_m{}^8 \rightarrow C_3H_2Cl_{6-n}{}^8F_n{}^8 \qquad (10)$$

$$0 \leq m^8 \leq 3 \; 2 \leq n^8 \leq 6, \; m^8 < n^8$$

The chlorine-containing 2,2-halogenopropane ($C_3H_2Cl_{6-m}{}^8F_m{}^8$ wherein $0 \leq m^8 \leq 3$) to be used as the starting material includes 1,1,1,2,2,3-hexachloropropane (R-230ab), 1,1,2,2,3,3-hexachloropropane (R-230aa), 1,1,1,2,3-pentachloro-2-fluoropropane (R-231bb), 1,1,1,3-tetrachloro-2,2-difluoropropane (R-232cb), 1,1,3,3-tetrachloro-2,2-difluoropropane (R-232ca) and 1,1,3-trichloro-1,2,2-trifluoropropane (R-233cb). These are known compounds.

The 2,2-difluoropropane ($C_3H_2Cl_{6-n}{}^8F_n{}^8$ wherein $2 \leq n^8 \leq 6$ and $m^8 < n^8$) to be formed by the reaction includes 1,1,3,3-tetrachloro-2,2-difluoropropane (R-232ca), 1,1,3-trichloro-1,2,2-trifluoropropane (R-233cb), 1,1,3-trichloro-2,2,3-trifluoropropane (R-233ca), 1,1-dichloro-1,2,2,3-tetrafluoropropane (R-234cd), 1,3-dichloro-1,1,2,2-tetrafluoropropane (R-234cc), 1,1-dichloro-2,2,3,3-tetrafluoropropane (R-234cb), 1,3-dichloro-1,2,2,3-tetrafluoropropane (R-234ca), 1-chloro-1,1,2,2,3-pentafluoropropane (R-235cc), 3-chloro-1,1,1,2,2-pentafluoropropane (R-235cb), 1-chloro-1,2,2,3,3-pentafluoropropane (R-235ca), 1,1,1,2,2,3-hexafluoropropane (R-236cb) and 1,1,2,2,3,3-hexafluoropropane (R-236ca). These products can be separated by a usual method such as fractional distillation.

$$C_3H_3Cl_{5-m}{}^8F_m{}^9 \rightarrow C_3H_3Cl_{5-n}{}^9F_n{}^9 \qquad (11)$$

$$0 \leq m^9 \leq 2 \; 2 \leq n^9 \leq 5, \; m^9 < n^9$$

The chlorine-containing 2,2 halogenopropane ($C_3H_3Cl_{5-m}{}^9F_m{}^9$ wherein $0 \leq m^9 \leq 2$) to be used as the starting material includes 1,1,2,2,3-pentachloropropane (R-240aa), 1,1,1,2,2-pentachloropropane (R-240ab), 1,1,2,3-tetrachloro-2-fluoropropane (R-241ba), 1,1,1,2-tetrachloro-2-fluoropropane (R-241bb), 1,1,3 trichloro-2,2-difluoropropane (R-242ca) and 1,1,1-trichloro-2,2-difluoropropane (R-242cb).

The 2,2-difluoropropane ($C_3H_3Cl_{5-n}{}^9F_n{}^9$ wherein $2 \leq n^9 \leq 5$) to be formed by the reaction includes 1,1,3-trichloro-2,2-difluoropropane (R-242ca), 1,1,1-trichloro-2,2-difluoropropane (R-242cb), 1,3-dichloro-1,2,2-trifluoropropane (R-243ca), 1,1-dichloro-2,2,3-trifluoropropane (R-243cb), 1,1-dichloro-1,2,2-trifluoropropane (R-243cc), 1-chloro-2,2,3,3-tetrafluoropropane (R-244ca), 1-chloro-1,2,2-tetrafluoropropane (R-244cc) and 1,1,1,2,2-pentafluoropropane (R-245cb). These products can be separated by a usual method such as fractional distillation.

$$C_3H_4Cl_{4-m}{}^{10}F_m{}^{10} \rightarrow C_3H_4Cl_{4-n}{}^{10}F_n{}^{10} \qquad (12)$$

$$0 \leq m^{10} \leq 1 \; 2 \leq n^{10} \leq 4$$

The chlorine-containing 2,2-halogenopropane ($C_3H_4Cl_{4-m}{}^{10}F_m{}^{10}$ wherein $0 \leq m^{10} \leq 1$) to be used as the starting material includes 1,2,2,3-tetrachloropropane (R-250aa), 1,1,2,2-tetrachloropropane (R-250ab), 1,2,3-trichloro-2-fluoropropane (R-251ba) and 1,1,2-trichloro-2-fuoropropane (R-251bb). These are known compounds.

The 2,2-difluoropropane ($C_3H_4Cl_{4-n}{}^{10}F_n{}^{10}$ wherein $2 \leq n^{10} \leq 4$) to be formed by the reaction includes 1,3-dichloro-2,2-difluoropropane (R-252ca), 1,1-dichloro-2,2-difluoropropane (R-252cb), 1-chloro-2,2,3-trifluoropropane (R-253ca), 1-chloro-1,2,2-trifluoropropane (R-253cb) and 1,1,2,2-tetrafluoropropane (R-254cb). These products can be separated by a usual method such as fractional distillation.

Now, the present invention will be described in further detail with reference to Examples. However, it should be understood that the present invention is by no means restricted by such specific Examples.

EXAMPLE 1-1

Into a 1 l Hastelloy C autoclave, 500 g of 1,1,1,2,2,3,3,3-octachloropropane ($CCl_3CCl_2CCl_3$ R-210aa), 50 g of tantalum pentafluoride and 300 g of hydrogen fluoride were charged. Then, the temperature was raised to 150° C., and hydrogen fluoride was fed in at a rate of 50 g per hour over a period of 3 hours. The reaction was conducted for 20 hours at this state while keeping the reaction temperature at this level. The reaction products were collected in a trap cooled at −78° C. The composition after removing acidic components from the collected product, was analyzed by gas chromatography and by $^{19}F$-NMR. As the results, it was confirmed that fluorine-containing chlorofluoropropanes such as $CF_3CClFCClFCClF_2$ (R-215ba), $CCl_2FCClFCClF_2$ (R-214ba), $CClF_2CCl_2CClF_2$ (R-214aa), $CCl_2FCClFCCl_2F$ (R-213ba), $CClF_2CCl_2CCl_2F$ (R-213aa), $CCl_2FCClFCCl_3$ (R-212ba) and $CCl_2F_2CCl_2CCl_2F$ (R-212aa), were formed in a certain amounts in addition to $CF_3CF_2CClF_2$ (R-217ca), $CF_3CF_2CCl_2F$ (R-216cb), $CClF_2CF_2CClF_2$ (R-216ca), CClF$_2$CF$_2$CCl$_2$F (R-215ca) and CCl$_2$FCF$_2$CCl$_2$F (R-214ca) which have a difluoromethylene group. The results are shown in Table 1-1.

TABLE 1-1

| Fluorination of R-210aa | |
|---|---|
| Conversion of R-210aa | 49% |
| Selectivity for R-217 | 2% |
| (for R-217ca) | (1%) |
| Selectivity for R-216 | 3% |
| (for R-216ca) | (1%) |
| (for R-216cb) | (1%) |
| Selectivity for R-215 | 12% |
| (for R-215ca) | (5%) |
| Selectivity for R-214 | 42% |
| (for R-214ca) | (2%) |
| Selectivity for R-213 | 27% |
| Selectivity for R-212 | 11% |
| Selectivity for others | 3% |

EXAMPLE 1-2

The reaction was conducted in the same manner as in Example 1-1 except that 500 g of 1,1,1,2,3,3,3-heptacholoro-2-fluoropropane (R-211ba) was used in place of 1,1,1,2,2,3,3,3-octachloropropane (R-210aa), 50 g of niobium pentachloride was used in place of tantalum pentafluoride and the reaction temperature was changed to 120° C. As the results, it was confirmed that chlorofluoropropanes such as CF$_3$CClFCClF$_2$ (R-216ba), CClF$_2$CClFCClF$_2$ (R-215ba), CCl$_2$FCClFCClF$_2$ (R-214ba), CCl$_2$FCClFCCl$_2$F (R-213ba) and CCl$_2$FCClFCCl$_3$ (R-212ba), were formed in certain amounts in addition to CF$_3$CF$_2$CClF$_2$ (Rca), CF$_3$CF$_2$CCl$_2$F (R-216cb), CClF$_2$CF$_2$CClF$_2$ (R-216ca), CClF$_2$CF$_2$CCl$_2$F (R-215ca) and CCl$_2$FCF$_2$CCl$_2$F (R-214ca) which have a difluoromethylene group. The results are shown in

TABLE 1-2

| Fluorination of R-211ba | |
|---|---|
| Conversion of R-211ba | 77% |
| Selectivity for R-217 | 2% |
| (for R-217ca) | (1%) |
| Selectivity for R-216 | 5% |
| (for R-216ca) | (2%) |
| (for R-216cb) | (1%) |
| Selectivity for R-215 | 21% |
| (for R-215ca) | (8%) |
| Selectivity for R-214 | 38% |
| (for R-214ca) | (16%) |
| (for R-214cb) | (2%) |
| Selectivity for R-213 | 17% |
| (for R-213cb) | (8%) |
| Selectivity for R-211 | 13% |
| Selectivity for others | 4% |

EXAMPLE 1-3

The reaction was conducted in the same manner as in Example 1-1 except that 500 g of 1,1,1,3,3,3-hexachloro-2,2-difluoropropane (R-212ca) was used in place of 1,1,1,2,2,3,3,3-octachloropropane (R-210aa), 50 g of antimony pentachloride was used in place of tantalum pentafluoride and the reaction temperature was changed to 120° C. As the results, it was confirmed that chlorofluoropropanes having a difluoromethylene group such as CF$_3$CF$_2$CClF$_2$ (R-217ca), CClF$_2$CF$_2$CClF$_2$ (R-216ca), CClF$_2$CF$_2$CCl$_2$F (R-215ca) and CCl$_2$FCF$_2$CCl$_2$F (R-214ca), were formed in certain amounts. The results are shown in Table 1-3.

TABLE 1-3

| Fluorination of R-212ca | |
|---|---|
| Conversion of R-212ca | 63% |
| Selectivity for R-217 | 2% |
| (for R-217ca) | (2%) |
| Selectivity for R-216 | 8% |
| (for R-216ca) | (7%) |
| (for R-216cb) | (1%) |
| Selectivity for R-215 | 20% |
| (for R-215ca) | (19%) |
| (for R-215cb) | (1%) |
| Selectivity for R-214 | 52% |
| (for R-214ca) | (50%) |
| (for R-214cb) | (2%) |
| Selectivity for R-213 | 17% |
| (for R-213ca) | (17%) |
| Selectivity for others | 1% |

EXAMPLE 1-4

The reaction was conducted in the same manner as in Example 1-1 except that 500 g of 1,1,1,3,3-pentachloro-2,2 difluoropropane (R-213ca) was used in place of 1,1,1,2,2,3,3,3-octachloropropane (R-210aa) and the reaction temperature was changed to 130° C. As the results, it was confirmed that chlorofluoropropanes having a difluoromethylene group such as CF$_3$CF$_2$CClF$_2$ (R217ca), CClF$_2$CF$_2$CClF$_2$ (R-216ca), CClF$_2$CF$_2$CCl$_2$F (R-215ca) and CCl$_2$FCF$_2$CCl$_2$F (R-214ca), were formed in certain amounts. The results are shown in Table 1-4.

TABLE 1-4

| Fluorination of R-213ca | |
|---|---|
| Conversion of R-213ca | 88% |
| Selectivity for R-217 | 4% |
| (for R-217ca) | (4%) |
| Selectivity for R-216 | 19% |
| (for R-216ca) | (17%) |
| (for R-216cb) | (2%) |
| Selectivity for R-215 | 30% |
| (for R-215ca) | (29%) |
| (for R-215cb) | (1%) |
| Selectivity for R-214 | 46% |
| (for R-214ca) | (44%) |
| (for R-214cb) | (2%) |
| Selectivity for others | 1% |

EXAMPLE 1-5

The reaction was conducted in the same manner as in Example 1-1 except that 500 g of 1,1,3,3-tetrachloro-1,2,2,3-tetrafluoropropane (R-214ca) was used in place of 1,1,1,2,2,3,3,3-octachloropropane (R-210aa) and the reaction temperature was changed to 130° C. As the results, it was confirmed that fluoropropanes and chlorofluoropropanes having a difluoromethylene group such as CF$_3$CF$_2$CF$_3$ (R-218ca), CF$_3$CF$_2$CClF$_2$ (R-217ca), CClF$_2$CF$_2$CClF$_2$ (R-216ca), CF$_3$CF$_2$CCl$_2$F (R-216cb) and CClF$_2$CF$_2$CCl$_2$F (R-215ca), were formed in certain amounts. The results are shown in Table 1-5.

TABLE 1-5

| Fluorination of R-214ca | |
|---|---|
| Conversion of R-214ca | 92% |
| Selectivity for R-218ca | 2% |
| Selectivity for R-217ca | 14% |
| Selectivity for R-216 | 44% |
| (for R-216ca) | (41%) |
| (for R-216cb) | (3%) |
| Selectivity for R-215 | 33% |

TABLE 1-5-continued

| Fluorination of R-214ca | |
| --- | --- |
| Conversion of R-214ca | 92% |
| (for R-215ca) | (31%) |
| (for R-215cb) | (2%) |
| Selectivity for others | 7% |

EXAMPLE 1-6

The reaction was conducted in the same manner as in Example 1 1 except that 500 g of 1,1,1,3-tetrachloro-2,2,3,3-tetrafluoropropane (R-214cb) was used in place of 1,1,1,2,2,3,3,3-octachloropropane (R-210aa) and the reaction temperature was changed to 110° C. As the results, it was confirmed that fluoropropanes and chlorofluoropropanes having a difluoromethylene group such as $CF_3CF_2CF_3$ (R-218ca), $CF_3CF_2CClF_2$ (R-217ca), $CClF_2CF_2CClF_2$ (R-216ca), $CF_3CF_2CCl_2F$ (R-216cb) and $CClF_2CF_2CCl_2F$ (R-215ca), were formed in certain amounts. The results are shown in Table 1-6.

TABLE 1-6

| Fluorination of R-214cb | |
| --- | --- |
| Conversion of R-214cb | 72% |
| Selectivity for R-218ca | 1% |
| Selectivity for R-217ca | 10% |
| Selectivity for R-216 | 34% |
| (for R-216ca) | (31%) |
| (for R-216cb) | (3%) |
| Selectivity for R-215 | 52% |
| (for R-215ca) | (51%) |
| (for R-215cb) | (1%) |
| Selectivity for others | 3% |

EXAMPLE 1-7

The reaction was conducted in the same manner as in Example 1 1 except that 500 g of 1,1,3-trichloro-1,2,2,3,3-pentafluoropropane (R-215ca) was used instead of 1,1,1,2,2,3,3,3-octachloropropane (R-210aa) and the reaction temperature was changed to 110° C. As the results, it was confirmed that fluoropropanes and chlorofluoropropanes having a difluoromethylene group such as $CF_3CF_2CF_3$ (R-218ca), $CF_3CF_2CClF_2$ (R-217ca), $CClF_2CF_2CClF_2$ (R-216ca) and $CF_3CF_2CCl_2F$ (R-216cb), were formed in certain amounts. The results are shown in Table 1-7.

TABLE 1-7

| Fluorination of R-215ca | |
| --- | --- |
| Conversion of R-215ca | 68% |
| Selectivity for R-218ca | 2% |
| Selectivity for R-217ca | 11% |
| Selectivity for R-216 | 84% |
| (for R-216ca) | (80%) |
| (for R-216cb) | (4%) |
| Selectivity for others | 3% |

EXAMPLE 1-8

The reaction was conducted in the same manner as in Example 1 1 except that 500 g of 1,1,1-trichloro-2,2,3,3,3-pentafluoropropane (R-215cb) was used in place of 1,1,1,2,2,3,3,3-octachloropropane (R-210aa). As the results, fluoropropanes and chlorofluoropropanes having a difluoromethylene group such as $CF_3CF_2CF_3$ (R-218ca), $CF_3CF_2CClF_2$ (R-217ca) and $CF_3CF_2CCl_2F$ (R-216cb), were formed in certain amounts. The results are shown in Table 1-8.

TABLEL 1-8

| Fluorination of R-215cb | |
| --- | --- |
| Conversion of R-215cb | 72% |
| Selectivity for R-218ca | 5% |
| Selectivity for R-217ca | 21% |
| Selectivity for R-216cb | 67% |
| Selectivity for others | 7% |

EXAMPLE 2-1

Into a 1 1 Hastelloy C autoclave, 500 g of 1,1,1,2,2,3,3,3-heptachloropropane ($CCl_3CCl_2CHCl_2$ R-220aa) and 50 g of antimony pentachloride were charged. The temperature was raised to 100° C. while hydrogen fluoride was supplied at a rate of 50 g per hour over a period of 5 hours. Then, hydrogen fluoride was further fed in at a rate of 50 g per hour over a period of 3 hours. The reaction was conducted at this state for 20 hours while keeping the reaction temperature at this level. The reaction products were collected in a trap cooled at −78° C. The composition after removal of acid components from the collected products, was analyzed by gas chromatography and by 19F-NMR. As the results, it was confirmed that monohydroheptahalogenopropanes having at least 2 fluorine atoms such as $CF_3CClFCHClF$ (R-225ba), $CHClFCCl_2CF_3$ (R-224aa), $CHCl_2CClFCF_3$ (R-224ba) and $CF_3CCl_2CHCl_2$ (R-223aa), were formed in addition to monohydroheptahalogenopropanes having a difluoromethylene group such as $CF_3CF_2CHClF$ (R-226ca), $CF_3CF_2CHCl_2$ (R-225ca), $CCl_2FCF_2CHClF$ (R-224cb) and $CCl_2FCF_2CHCl_2$ (R-223ca). The results are show in Table 2-1.

TABLE 2-1

| Fluorination of R-220aa | |
| --- | --- |
| Conversion of R-220aa | 58% |
| Selectivity for R-226 | 2% |
| (for R-226ca) | (1%) |
| Selectivity for R-225 | 7% |
| (for R-225ca) | (5%) |
| Selectivity for R-224 | 21% |
| (for R-224cb) | (2%) |
| Selectivity for R-223 | 28% |
| (for R-223ca) | (1%) |
| Selectivity for R-222 | 30% |
| Selectivity for others | 12% |

EXAMPLE 2-2

The reaction was conducted in the same manner as in Example 2-1 except that 500 g of 1,1,1,2,3,3-hexachloro-2-fluoropropane ($CCl_3CClFCHCl_2$: R-221ba) was used in place of 1,1,1,2,2,3,3-heptachloropropane ($CCl_3CCl_2CHCl_2$: R-220aa), 50 g of niobium pentachloride was used in place of antimony pentachloride and the reaction temperature was changed to 120° C. As the results, it was confirmed that monohydroheptahalogenopropanes having at least 2 fluorine atoms such as $CF_3CClFCHClF$ (R-225ba) and $CClF_2CClFCHClF$ (R-224bb) were formed in addition to monohydroheptahalogenopropanes having a difluoromethylene group such as $CF_3CF_2CHClF$ (R-226ca), $CF_3CF_2CHCCl_2$ (Rca) and $CCl_2FCF_2CHClF$ (R-224cb). The results are shown in Table 2-2.

TABLE 2-2

| Fluorination of R-221ba | |
|---|---|
| Conversion of R-221ba | 85% |
| Selectivity for R-226 | 3% |
| (for R-226ca) | (2%) |
| Selectivity for R-225 | 9% |
| (for R-225ca) | (6%) |
| Selectivity for R-224 | 30% |
| (for R-224cb) | (2%) |
| Selectivity for R-223 | 29% |
| Selectivity for R-222 | 17% |
| Selectivity for others | 12% |

EXAMPLE 2-3

The reaction was conducted in the same manner as in Example 2-1 except that 500 g of 1,1,3,3-pentachloro-2,2-difluoropropane (R-222ca) was used in place of 1,1,1,2,2,3,3-heptachloropropane ($CCl_3CCl_2CHCl_2$: R-220aa), 50 g of niobium pentachloride was used in place of antimony pentachloride and the reaction temperature was changed to 120° C. As the results, it was confirmed that monohydroheptahalogenopropanes having a difluoromethylene group such as $CF_3CF_2CHF_2$ (R-227ca), $CF_3CF_2CHClF$ (R-226ca), $CF_3CF_2CHCl_2$ (R-225ca), $CClF_2CF_2CHClF$ (R-225cb), $CClF_2CF_2CHCl_2$ (R-224ca), $CCl_2FCF_2CHClF$ (R-224cb) and $CCl_2FCF_2CHCl_2$ (R-223ca), were formed. The results are shown in Table 2-3.

TABLE 2-3

| Fluorination of R-222ca | |
|---|---|
| Conversion of R-222ca | 78% |
| Selectivity for R-227ca | 1% |
| Selectivity for R-226 | 3% |
| (for R-226ca) | (2%) |
| (for R-226cb) | (1%) |
| Selectivity for R-225 | 12% |
| (for R-225ca) | (8%) |
| (for R-225cb) | (3%) |
| (for R-225cc) | (1%) |
| Selectivity for R-224 | 37% |
| (for R-224ca) | (25%) |
| (for R-224cb) | (11%) |
| (for R-224cc) | (1%) |
| Selectivity for R-223 | 46% |
| (for R-223ca) | (35%) |
| (for R-223cb) | (11%) |
| Selectivity for others | 1% |

EXAMPLE 2-4

The reaction was conducted in the same manner as in Example 2-1 except that 500 g of 1,1,3,3-tetrachloro-1,2,2-trifluoropropane (R-223ca) was used in place of 1,1,1,2,2,3,3-heptachloropropane ($CCl_3CCl_2CHCl_2$ R-220aa) and 50 g of niobium pentachloride was used in place of antimony pentachloride. As the results, monohydroheptahalogenopropanes having a difluoromethylene group such as $CF_3CF_2CHF_2$ (R-227ca), $CF_3CF_2CHClF$ (R-226ca), $CF_3CF_2CHCl_2$ (R-225ca), $CClF_2CF_2CHClF$ (R-225cb), $CClF_2CF_2CHCl_2$ (R-224ca) and $CCl_2FCF_2CHClF$ (R-224cb), were formed. The results are shown in Table 2-4.

TABLE 2-4

| Fluorination of R-223ca | |
|---|---|
| Conversation of R-223ca | 88% |
| Selectivity for R-227ca | 2% |
| Selectivity for R-226 | 3% |
| (for R-226ca) | (3%) |
| (for R-226cb) | (1%) |
| Selectivity for R-225 | 30% |
| (for R-225ca) | (21%) |
| (for R-225cb) | (7%) |
| (for R-225cc) | (1%) |
| Selectivity for R-224 | 64% |
| (for R-224ca) | (46%) |
| (for R-224cb) | (17%) |
| (for R-224cc) | (1%) |
| Selectivity for others | 1% |

EXAMPLE 2-5

The reaction was conducted in the same manner as in Example 2-1 except that 500 g of 1,1,1,3-tetrachloro-2,2,3-trifluoropropane (R-223cb) was used in place of 1,1,1,2,2,3,3-heptachloropropane ($CCl_3CCl_2CHCl_2$: R-220aa) and 50 g of niobium pentachloride was used in place of anitimony pentachloride. As the results, monohydroheptahalogenopropanes having a difluoromethylene group such as $CF_3CF_2CHF_2$ (R-227ca), $CF_3CF_2CHClF$ (R-226ca), $CClF_2CF_2CHCClF$ (R-225cb) and $CCl_2FCF_2CHClF$ (R-224cb), were formed. The results are shown in Table 2-5.

TABLE 2-5

| Fluorination of R-223cb | |
|---|---|
| Conversion of R-223cb | 72% |
| Selectivity for R-227ca | 1% |
| Selectivity for R-226 | 2% |
| (for R-226ca) | (2%) |
| Selectivity for R-225 | 39% |
| (for R-225cb) | (37%) |
| (for R-225cc) | (2%) |
| Selectivity for R-224 | 57% |
| (for R-224cb) | (57%) |
| (for R-224cc) | (1%) |
| Selectivity for others | 1% |

EXAMPLE 2-6

The reaction was conducted in the same manner as in Example 2-1 except that 500 g of 1,3,3-trichloro-1,1,2,2-tetrafluoropropane (R-224ca) was used in place of 1,1,1,2,2,3,3-heptachloropropane ($CCl_3CCl_2CHCl_2$ R-220aa) and 50 g of niobium pentachloride was used in place of antimony pentachloride. As the results, it was confirmed that monohydroheptahalogenopropanes having a difluoromethylene group such as $CF_3CF_2CHF_2$ (R-227ca), $CF_3CF_2CHClF$ (R-226ca), $CClF_2CF_2CHF_2$ (R-226cb), $CF_3CF_2CHCl_2$ (R-225ca) and $CClF_2CF_2CHClF$ (R-225cb), were formed. The results are shown in Table 2-6.

TABLE 2-6

| Fluorination of R-224ca | |
|---|---|
| Conversion of R-224ca | 65% |
| Selectivity of R-227ca | 1% |
| Selectivity of R-226 | 5% |
| (for R-226ca) | (4%) |
| (for R-226cb) | (1%) |
| Selectivity for R-225 | 94% |
| (for R-225ca) | (83%) |
| (for R-225cb) | (10%) |
| (for R-225cc) | (1%) |
| Selectivity for others | 1% |

EXAMPLE 2-7

The reactin was conducted in the same manner as in Example 2-1 except that 500 g of 1,1,3-trichloro-1,2,2,3-tetrafluoropropane (R-224cb) was used in place of 1,1,1,2,2,3,3-heptachloroproane ($CCl_3CCl_2CHCl_2$: R-220aa), and 50 g of niobium pentachloride was used in place of antimony pentachloride. As the results, it was confirmed that monohydroheptahalogenopropanes having a difluoromethylene group such as $CF_3CF_2CHF_2$ (R-227ca), $CF_3CF_2CHClF$ (R-226ca), $CClF_2CF_2CHF_2$ (R-226cb) and $CClF_2CF_2CHClF$ (R-225cb), were formed. The results are shown in Table 2-7.

TABLE 2-7

| Fluorination of R-224cb | |
|---|---|
| Conversion of R-224cb | 68% |
| Selectivity of R-227ca | 1% |
| Selectivity of R-226 | 23% |
| (for R-226ca) | (19%) |
| (for R-226cb) | (4%) |
| Selectivity of R-225 | 69% |
| (for R-225cb) | (61%) |
| (for R-225cc) | (8%) |
| Selectivity for others | 7% |

EXAMPLE 2-8

The reaction was conducted in the same manner as in Example 2-1 except that 500 g of 1,1,1-trichloro-2,2,3,3-tetrafluoropropane (R-224cc) was used in place of 1,1,1,2,2,3,3-heptachloropropane ($CCl_3CCl_2CHCl_2$: R-220aa) and 50 g of niobium pentachloride was used in place of antimony pentachloride. As the results, it was confirmed that monohydroheptahalogenopropanes having a difluoromethylene group such as $CF_3CF_2CHF_2$ (R-227ca) and $CCl_2FCF_2CHF_2$ (R-225cc) were formed. The results are shown in Table 2-8.

TABLE 2-8

| Fluorination of R-224cc | |
|---|---|
| Conversion of R-224cc | 88% |
| Selectivity of R-227ca | 5% |
| Selectivity of R-226cb | 28% |
| Selectivity of R-225cc | 63% |
| Selectivity for others | 4% |

EXAMPLE 3-1

Into a 1 l Hastelloy C autoclave, 500 g of 1,1,1,2,2,3-hexachloropropane ($CCl_3CCl_2CH_2Cl$: R-230ab) and 50 g of antimony pentachloride, were charged. The temperature was raised to 100° C. while hydrogen fluoride was supplied at a rate of 50 g per hour over a period of 3 hours. Then, hydrogen fluoride was further fed in at a rate of 50 g per hour over a period of 3 hours. The reaction was conducted at this state for 20 hours while keeping the reaction temperature at this level. The reaction products were collected in a trap cooled at −78° C. The composition after removing acidic components from the collected products was analyzed by gas chromatography and by $^{19}F$-NMR. As the results, it was confirmed that dihydrohexahalogenopropanes having at least 2 fluorine atoms such as $CF_3CClFCH_2Cl$ (R-234bb), $CClF_2CClFCH_2Cl$ (R-233bc) and $CClF_2CCl_2CH_2Cl$ (R-232ab), were formed in addition to dihydrohexahalogenopropanes having a difluoromethylene group such as $CF_3CF_2CH_2Cl$ (R-235cb), $CClF_2CF_2CH_2Cl$ (R-234cc) and $CCl_2FCF_2CH_2Cl$ (R-233cb). The results are shown in Table 3-1.

TABLE 3-1

| Fluorination of R-230ab | |
|---|---|
| Conversion of R-230ab | 43% |
| Selectivity for R-235cb | 1% |
| Selectivity for R-234 | 32% |
| (for R-234cc) | (17%) |
| Selectivity for R-233 | 36% |
| (for R-233cb) | (2%) |
| Selectivity for R-232 | 23% |
| Selectivity for others | 8% |

EXAMPLE 3-2

The reaction was conducted in the same manner as in Example 3-1 except that 500 g of 1,1,2,2,3,3-hexachloropropane (R-230aa) was used in place of 1,1,1,2,2,3-hexachloropropane (R-230ab), 50 g of tantalum pentafluoride was used in place of antimony pentachloride and the reaction tempreature was changed to 120° C. As the results, it was confirmed that dihydrohexahalogenopropanes having at least 2 fluorine atoms such as $CHF_2CClFCClF$ (R-234ba), $CHClFCCl_2CHF_2$ (R-233aa), $CHClFCClFCHClF$ (R-233ba) and $CHF_2ClFCHCl_2$ (R-223bb), were formed in addition to dihydrohexahalogenopropanes having a difluoromethylene group such as $CHF_2CF_2CHClF$ (R-235ca), $CHClFCF_2CHClF$ (R-234ca), $CHCl_2CF_2CHF_2$ (R-234cb) and $CHCl_2CF_2CHClF$ (R-233ca). The results are shown in Table 3-2.

TABLE 3-2

| Fluorination of R-230aa | |
|---|---|
| Conversion of R-230aa | 68% |
| Selectivity for R-235 | 5% |
| (for R-235ca) | (3%) |
| Selectivity for R-234 | 22% |
| (for R-234cb) | (12%) |
| (for R-234ca) | (3%) |
| Selectivity for R-233 | 29% |
| (for R-233ca) | (2%) |
| Selectivity for R-232 | 33% |
| Selectivity for others | 11% |

EXAMPLE 3-3

The reaction was conducted in the same manner as in Example 3-1 except that 500 g of 1,1,1,2,3-pentachloro-2-fluoropropane (R-231bb) was used in place of 1,1,1,2,2,3-hexachloropropane (R-230ab), 50 g of tantalum pentafluoride was used in place of antimony penthachloride and the reaction temperature was changed to 120° C. As the results, it was confirmed that dihydrohexahalogenopropanes having at least 2 fluorine atoms such as $CF_3CClFCH_2Cl$ (R-234bb), $CClF_2CClFCH_2Cl$ (R-233bc) and $CCl_2FCClFCH_2Cl$ (R-232bb), were formed in addition to dihydrohexahalogenopropanes having a difluoromethylene group such as $CF_3CF_2CH_2Cl$ (R-235cb), $CClF_2CF_2CH_2Cl$ (R-234cc) and $CCl_2FCF_2CH_2Cl$ (R-233cb). The results are shown in Table 3-3.

TABLE 3-3

| Fluorination of R-231bb | |
|---|---|
| Conversion of R-231bb | 73% |
| Selectivity for R-235cb | 8% |
| Selectivity for R-234 | 49% |

TABLE 3-3-continued

| Fluorination of R-231bb | |
|---|---|
| Conversion of R-231bb | 73% |
| (for R-234cc) | (27%) |
| Selectivity for R-233 | 31% |
| (for R-233cb) | (13%) |
| Selectivity for R-232 | 3% |
| Selectivity for others | 9% |

EXAMPLE 3-4

The reaction was conducted in the same manner as in Example 3-1 except that 500 g of 1,1,1,3-tetrachloro-2,2-difluoropropane (R-232cb) was used in place of 1,1,1,2,2,3-hexachloropropane (R-230ab) and the reaction temeprature was changed to 120° C. As the results, it was confirmed that dihydrohexahalogenopropanes having a difluoromethylene group such as $CF_3CF_2CH_2Cl$ (R-235cb), $CClF_2CF_2CH_2Cl$ (R-234cc) and $CCl_2FCF_2CH_2Cl$ (R-233cb), were formed. The results are shown in Table 3-4.

TABLE 3-4

| Fluorination of R-232cb | |
|---|---|
| Conversion of R-232cb | 62% |
| Selectivity for R-235cb | 2% |
| Selectivity for R-234cc | 53% |
| Selectivity for R-233cb | 38% |
| Selectivity for others | 7% |

EXAMPLE 3-5

The reaction was conducted in the same manner as in Example 3-1 except that 500 g of 1,1,3,3-tetrachloro-2,2-difluoropropane (R-232ca) was used in place of 1,1,1,2,2,3-hexachloropropane (R-230ab), 50 g of tantalum pentafluoride was used in place of antimony pentachloride and the reaction temeprature was changed to 130° C. As the results, it was confirmed that dihydrohexahalogenopropanes having a difluoromethylene group such as $CHF_2CF_2CHF_2$ (R-236ca), $CHF_2CF_2CHClF$ (R-235ca), $CHClFCF_2CHClF$ (R-234ca) and $CHCl_2CF_2CHF_2$ (R-234cb), were formed. The results are shown in Table 3-5.

TABLE 3-5

| Fluorination of R-232ca | |
|---|---|
| Conversion of R-232ca | 83% |
| Selectivity for R-236ca | 1% |
| Selectivity for R-235ca | 12% |
| Selectivity for R-234 | 32% |
| (for R-234cb) | (27%) |
| (for R-234ca) | (5%) |
| Selectivity for R-233ca | 46% |
| Selectivity for others | 9% |

EXAMPLE 3-6

The reaction was conducted in the same manner as in Example 3-1 except that 500 g of 1,1,1-trichloro-2,2,3-trifluoropropane (R-233cc) was used in place of 1,1,1,2,2,3-hexachloropropane (R-230ab) and the reaction temperature was changed to 120° C. As the results, it was confirmed that dihydrohexahalogenopropanes having a difluoromethylene group such as $CF_3CF_2CH_2F$ (R-236cb), $CClF_2CF_2CH_2F$ (R-235cc) and $CCl_2FCF_2CH_2F$ (R-234cd), were formed. The results are shown in Table 3-6.

TABLE 3-6

| Fluorination of R-233cc | |
|---|---|
| Conversion of R-233cc | 65% |
| Selectivity for R-236cb | 4% |
| Selectivity for R-235cc | 13% |
| Selectivity for R-234cd | 55% |
| Selectivity for others | 28% |

EXAMPLE 3-7

The reaction was conducted in the same manner as in Example 3-1 except that 500 g of 1,1,3-trichloro-1,2,2-trifluoropropane (R-233cb) was used in place of 1,1,1,2,2,3 hexachloropropane (R-230ab), 100 g of niobium pentachloride was used in place of antimony pentachloride and the reaction temperature was changed to 110° C. As the results, dihydrohexahalogenopropanes having a difluoromethylene group such as $CF_3CF_2CH_2Cl$ (R-235cb) and $CClF_2CF_2CH_2Cl$ (R-234cc), were formed. The results are shown in Table 3-7.

TABLE 3-7

| Fluorination of R-233cb | |
|---|---|
| Conversion of R-233cb | 79% |
| Selectivity for R-235cb | 17% |
| Selectivity for R-234cc | 82% |
| Selectivity for others | 1% |

EXAMPLE 3-8

The reaction was conducted in the same manner as in Example 3-1 except that 500 g of 1,1,3-trichloro-2,2,3-trifluoropropane (R-233ca) was used in place of 1,1,1,2,2,3-hexachloropropane (R-230ab), 50 g of tantalum pentafluoride was used in place of antimony pentachloride and reaction temperature was changed to 120° C. As the results, it was confirmed that dihydrohexahalogenopropanes having a difluoromethylene group such as $CHF_2CF_2CHF_2$ (R-236ca), $CHF_2CF_2CHClF$ (R-235ca), $CHClFCF_2CHClF$ (R-234ca) and $CHCl_2CF_2CHF_2$ (R-234cb), were formed. The results are shown in Table 3-8.

TABLE 3-8

| Fluorination of R-233ca | |
|---|---|
| Conversion of R-233ca | 91% |
| Selectivity for R-236ca | 3% |
| Selectivity for R-235ca | 41% |
| Selectivity for R-234 | 55% |
| (for R-234cb) | (43%) |
| (for R-234ca) | (12%) |
| Selectivity for others | 1% |

EXAMPLE 4-1

Into a 1 l Hastelloy C autoclave, 500 g of 1,1,2,2,3-pentachloropropane ($CHCl_2CCl_2CH_2Cl$: R-240aa) and 50 g of antimony pentachloride, were charged. The temperature was raised to 100° C. while hydrogen fluoride was supplied at a rate of 50 g/hr over a period of 3 hours. Then, hydrogen fluoride was further fed in at a rate of 50 g/hr over a period of 3 hours. The reaction was conducted at this state for 20 hours while keeping the reaction temperature at this level. The reaction products were collected in a trap cooled at −78° C. The composition after removing acidic components from the collected products, was analyzed by gas chromatography and by $^{19}$FNMR. As the results, it was confirmed that trihydropentahalogehopropanes having at least 2 fluorine atoms such as $CHF_2CClFCH_2Cl$ (R-243ba), $CHClFCClFCH_2Cl$ (R-242ba), $CHCl_2CClFCH_2Cl$ (R-241ba) and $CHClFCCl_2CH_2Cl$ (R-241aa), were formed in addition to trihydropentahalogenopropanes having a difluoromethylene group such as $CHF_2CF_2CH_2Cl$ (R-244ca), $CHClFCF_2CH_2Cl$ (R-243ca) and $CHCl_2CF_2CH_2Cl$ (R-242ca). The results are shown in Table 4-1.

TABLE 4-1

| Fluorination of R-240aa | |
|---|---|
| Conversion of R-240aa | 38% |
| Selectivity for R-244ca | 1% |
| Selectivity for R-243 | 22% |
| (for R-243ca) | (7%) |
| Selectivity for R-242 | 36% |
| (for R-242ca) | (2%) |
| Selectivity for R-241 | 33% |
| Selectivity for others | 8% |

EXAMPLE 4-2

The reaction was conducted in the same manner as in Example 4-1 except that 500 g of 1,1,1,2,2-pentachloropropane (R-240ab) was used in place of 1,1,2,2,3-pentachloropropane-(R-240aa), 50 g of tantalum pentafluoride was used in place of antimony pentachloride and the reaction temperature was changed to 120° C. As the results, it was confirmed that trihydropentahalogenopropanes having at least 2 fluroine atoms such as $CF_3CClFCH_3$ (R-243ba), $CClF_2CClFCH_3$ (R-243bc), $CF_3Cl_2CH_3$ (R-243ab), $CClF_2CClFCH_3$ (R-243bc) and $CClF_2CCl_2CH_3$ (R-242ac), were formed in addition to trihydropentahalogenopropanes having a difluoromethylene group such as $CF_3CF_2CH_3$ (R-245cb) and $CClF_2CF_2CH_3$ (R-244cc). The results are shown in Table 4-2.

TABLE 4-2

| Fluorination of R-240ab | |
|---|---|
| Conversion of R-240ab | 72% |
| Selectivity for R-245cb | 2% |
| Selectivity for R-244 | 12% |
| (for R-244cc) | (5%) |
| Selectivity for R-243 | 21% |
| Selectivity for R-242 | 43% |
| Selectivity for others | 22% |

EXAMPLE 4-3

The reaction was conducted in the same manner as in Example 4-1 except that 500 g of 1,1,2,3-tetrachloro-2-fluoropropane (R-241ba) was used in place of 1,1,2,2,3-pentachloropropane (R-240aa), 50 g of tantalum pentafluoride was used in place of antimony pentachloride and the reaction temperature was changed to 130° C. As the results, it was confirmed that trihydropentahalogenopropanes having at least fluorine atoms such as $CHF_2CClFCH_2Cl$ (R-243ba) and $CHClFCClFCH_2Cl$ (R-242ba) were formed in addition to trihydropentahalogenopropanes having a difluoromethylene group such as $CHF_2CF_2CH_2Cl$ (R-244ca), $CHClFCF_2CH_2Cl$ (R-243ca) and $CHCl_2CF_2CH_2Cl$ (R-242ca). The results are shown in Table 4-3.

TABLE 4-3

| Fluorination of R-241ba | |
|---|---|
| Conversion of R-241ba | 69% |
| Selectivity for R-244ca | 3% |
| Selectivity for R-243 | 55% |
| (for R-243ca) | (37%) |
| Selectivity for R-242 | 39% |
| (for R-242ca) | (5%) |
| Selectivity for others | 3% |

EXAMPLE 4-4

The reaction was conducted in the same manner as in Example 4-1 except that 500 g of 1,1,1,2-tetrachloro-2-fluoropropane (R-241bb) was used in place of 1,1,1,2,2,3-pentachloropropane (R-240aa), 50 g of niobium pentachloride was used in place of antimony pentachloride and the reaction temperature was changed to 130° C. As the results, it was confirmed that trihydropentahalogenopropanes having at least 2 fluorine atoms such as $CF_3CClFCH_3$ (R-244bb), $CClF_2CClFCH_3$ (R-243bc) and $CCl_2FCClFCH_3$ (R-242bc), were formed in addition to trihydropentahalogenopropanes having a difluoromethylene group such as $CF_3CF_2CH_3$ (R-245cb), $CClF_2CF_2CH_3$ (R-244cc), $CCl_2FCF_2CH_3$ (R-243cc) and $CCl_3CF_2CH_3$ (R-242cb). The results are shown in Table 4-4.

TABLE 4-4

| Fluorination of R-241bb | |
|---|---|
| Conversion of R-241bb | 73% |
| Selectivity for R-245cb | 3% |
| Selectivity for R-244 | 22% |
| (for R-244cc) | (12%) |
| Selectivity for R-243 | 46% |
| (for R-243cc) | (18%) |
| Selectivity for R-242 | 26% |
| (for R-242cb) | (3%) |
| Selectivity for others | 3% |

EXAMPLE 4-5

The reaction was conducted in the same manner as in Example 4-1 except that 500 g of 1,1,3-trichloro-2,2-difluoropropane (R-242ca) was used in place of 1,1,2,2,3-pentachloropropane (R-240aa), 50 g of tantalum pentafluoride was used in place of antimony pentachloride and the reaction temperature was changed to 110° C. The results are shown in Table 4-5.

TABLE 4-5

| Fluorination of R-242ca | |
|---|---|
| Conversion of R-242ca | 73% |
| Selectivity for R-244ca | 8% |
| Selectivity for R-243ca | 75% |
| Selectivity for others | 17% |

EXAMPLE 4-6

The reaction was conducted in the same manner as in Example 4-1 except that 500 g of 1,1,1-trichloro-2,2-difluoropropane (R-242cb) was used in place of 1,1,2,2,3-pentachloropropane (R-240aa) and the reaction temperature was changed to 110° C. The results are shown in Table 4-6.

TABLE 4-6

| Fluorination of R-242cb | |
|---|---|
| Conversion of R-242cb | 75% |
| Selectivity for R-245cb | 5% |
| Selectivity for R-244cc | 28% |
| Selectivity for R-243cc | 66% |
| Selectivity for others | 1% |

EXAMPLE 5-1

Into a 1 l Hastelloy C autoclave, 500 g of 1,2,2,3-tetrachloropropane (R-250aa) and 50 g of antimony pentachloride, were charged. The reaction was raised to 120° C. while hydrogen fluoride was fed in at a rate of 50 g/hr over a period of 3 hours. Then, hydrogen fluoride was supplied at a rate of 50 g/hr over a period of 3 hours. The reaction was conducted at this state for 20 hours while keeping the reaction temperature at this level. The reaction products were collected in a trap cooled at −78° C. The composition after removing acidic components from the collected products, was analyzed by gas chromatography and by $^{19}$F-NMR. As the results, it was confirmed that $CH_2ClCF_2CHCl$ (R-252ca) having a difluoromethylene group was formed. The results are shown in Table 5-1.

TABLE 5-1

| Fluorination of R-250aa | |
|---|---|
| Conversion of R-250aa | 46% |
| Selectivity for R-252ca | 12% |
| Selectivity for R-251ba | 84% |
| Selectivity for others | 4% |

EXAMPLE 5-2

The reaction was conducted in the same manner as in Example 5-1 except that 500 g of 1,1,2,2-tetrachloropropane (R-250ab) was used in place of 1,2,2,3-tetrachloropropane (R-250aa), 50 g of tantalum pentafluoride was used in place of antimony pentachloride and the reaction temperature was changed to 130° C. As the results, it was confirmed that tetrahydrotetrahalogenopropanes having at least 2 fluorine atoms such as $CHF_2CClFCH_3$ (R-253bb) and $CHClFCClFCH_3$ (R-252bb) were formed in addition to tetrahydrotetrahalogenopropanes having a difluoromethylene group such as $CHF_2CF_2CH_3$ (R-254cb), $CHClFCF_2CH_3$ (R-253cb) and $CHCl_2CF_2CH_3$ (R-252cb). The results are shown in Table 5-2.

TABLE 5-2

| Fluorination of R-250ab | |
|---|---|
| Conversion of R-250ab | 58% |
| Selectivity for R-254cb | 4% |
| Selectivity for R-253 | 22% |
| (for R-253cb) | (12%) |
| Selectivity for R-252 | 39% |
| (for R-252cb) | (10%) |
| Selectivity for R-251 | 33% |
| Selectivity for others | 2% |

EXAMPLE 5-3

The reaction was conducted in the same manner as in Example 5-1 except that 500 g of 1,2,3-trichloro-2-fluoropropane (R-251ba) was used in place of 1,2,2,3-tetrachloropropane (R-250aa), 100 g of niobium pentachloride was used in place of antimony pentachloride and the reaction temperature was changed to 100° C. As the results, it was confirmed that tetrahydrotetrahalogenopropanes having a difluoromethylene group such as $CH_2ClCF_2CH_2F$ (R-253ca) and $CH_2ClCF_2CH_2Cl$ (R-252ca), were formed. The results are shown in Table 5-3.

TABLE 5-3

| Fluorination of R-251ba | |
|---|---|
| Conversion of R-251ba | 79% |
| Selectivity for R-253ca | 3% |
| Selectivity for R-252ca | 86% |
| Selectivity for others | 11% |

EXAMPLE 5-4

The reaction was conducted in the same manner as in Example 5-1 except that 500 g of 1,1,2-trichloro-2-fluoropropane (R-251bb) was used in place of 1,2,2,3-tetrachloropropane (R-250aa), and 40 g of tantalum pentachloride was used in place of antimony pentachloride and the reaction temperature was changed to 120° C. As the results, it was confirmed that tetrahydrotetrahalogenopropanes having at least 2 fluorine atoms such as $CHF_2CClFCH_3$ (R-253bb) and $CHClFCClFCH_3$ (R-252bb), were formed in addition to tetrahydrotetrahalogenopropanes having a difluoromethylene group such as $CHF_2CF_2CH_3$ (R-254cb), $CHClFCF_2CH_3$ (R-253cb) and $CHCl_2CF_2CH_3$ (R-252bb). The results are shown in Table 5-4.

TABLE 5-4

| Fluorination of R-251bb | |
|---|---|
| Conversion of R-251bb | 73% |
| Selectivity for R-254cb | 3% |
| Selectivity for R-253 | 14% |
| (for R-253cb) | (8%) |
| Selectivity for R-252 | 74% |
| (for R-252cb) | (37%) |
| Selectivity for others | 9% |

PREPARATION EXAMPLE 1

1,200 g of $Cr(NO_3)_3.9H_2O$ and 100 g of $Mg(NO_3)_2.6H_2O$ were dissolved in 2.5 l of water, and this solution and 2,000 g of 28% ammonium hydroxide aqueous solution were added to 4 l of hot water under stirring to give precipitates of the hydroxides. The precipitates were collected by filtration, washed with pure water, dried and then sintered at 450° C. for 5 hours to give the powder of the oxides. The powder was shaped into a cylindrical tablet having a diameter of 5 mm and a height of 5 mm by a tabletting machine. The catalyst thereby obtained was activated by fluorinating at a temperature of from 250 to 400° C. in a gas stream of hydrogen fluoride/nitrogen mixture before using it in the reaction.

PREPARATION EXAMPLE 2

1,100 g of guaranteed reagent of $Al(NO_3)_3.9H_2O$, 125 g of $Cr(NO_3)_3.9H_2O$ and 40 g of $Mg(NO_3)_2.6H_2O$, were dissolved in 2.5 l of water, and this solution and 2,000 g of 28% ammonium hydroxide aqueous solution were added to 4 l of hot water to give precipitates of the hydroxides. The precipitates were collected by filtration, washed with pure water, dried and sintered at 450° C. for 5 hours to give the powder of the oxides. The powder was shaped into a cylindrical tablet having a diameter of 5 mm and a height of 5 mm by a tabletting machine. The catalyst thereby obtained was activated by fluorinating at a temperature of from 250° to 400° C. in a gas stream of hydrogen fluoride/nitrogen mixture before using it in the reaction.

PREPARATION EXAMPLES 3 TO 6

The catalysts were prepared in the same manner as in Preparation Example 2 except that 40 g of $Ba(NO_3)_2$, 50 g of $Sr(NO_3)_2$, 40 g of $Ca(NO_3)_2.4H_2O$ and 60 g of $Mn(NO_3)_2.4H_2O$ were used in place of $Mg(NO_3)_2.6H_2O$, respectively.

PREPARATION EXAMPLE 7

The catalyst was prepared in the same manner as in Preparation Example 2 except that 300 g of $Fe(NO_3)_2.9H_2O$ and 900 g of $Al(NO_3)_3.9H_2O$ were used in place of $Al(NO_3)_3.9H_2O$, $Cr(NO_3)_3.9H_2O$ and $Mg(NO_3)_2.6H_2O$.

PREPARATION EXAMPLE 8

The catalyst was prepared in the same manner as in Preparation Example 2 except that 600 g of $Fe(NO_3)_2.9H_2O$ and 150 g of $Cr(NO_3)_3.9H_2O$ were used in place of $Al(NO_3)_3.9H_2O$, $Cr(NO_3)_3.9H_2O$ and $Mg(NO_3)_2.6H_2O$.

PREPARATION EXAMPLE 9

200 g of $AlCl_3$ was dissolved in 2 l of water. To this solution, 1,000 g of commercially available γ-alumina was added, and then it was dried to remove moisture. Further, the catalyst thereby obtained was activated by the same activating method as in Preparation Example 1.

PREPARATION EXAMPLE 10

The catalyst was prepared in the same manner as in Preparation Example 9 except that 200 g of $CrCl_3.6H_2O$ was used in place of $AlCl_3$. Further, the catalyst thereby obtained was activated by the same activating method as in Preparation Example 1.

PREPARATION EXAMPLE 11

The catalyst was prepared in the same manner as in Preparation Example 9 except that 200 g of $MnCl_2.4H_2O$ was used in place of $AlCl_3$. Further, the catalyst thereby obtained was activated by the same activating method as in Preparation Example 1.

PREPARATION EXAMPLE 12

The catalyst was prepared in the same manner as in Preparation Example 9 except that 200 g of $NiCl_2.6H_2O$ was used in place of $AlCl_3$. Further, the catalyst thereby obtained was activated by the same activating method as in Preparation Example 1.

PREPARATION EXAMPLE 13

The catalyst was prepared in the same manner as in Preparation Example 9 except that 200 g of $CoCl_2.6H_2O$ was used in place of $AlCl_3$. Further, the catalyst thereby obtained was activated by the same activating method as in Preparation Example 1.

PREPARATION EXAMPLE 14

The catalyst was prepared in the same manner as in Preparation Example 9 except that 1,000 g of commercial available granulated activated carbon useful as a support for the catalyst was used in place of γ-alumina. Further, the catalyst thereby obtained was activated by the same activating method as in Preparation Example 1.

EXAMPLE 6-1

An Inconnel 600 U-shaped reaction tube having an inner diameter of 2.54 cm and a length of 100 cm packed with 200 ml of fluorination catalyst prepared in the same manner as in Preparation Example 1, was used as a fluorination reactor. To the reactor kept at a temperature of 350° C., gasified 1,1,1-trichloropentafluoropropane, oxygen and hydrogen fluoride were fed in at a rate of 50 ml/minutes, 2 ml/minutes and 100 ml/minutes, respectively and reacted. The reaction products were collected in a trap cooled at $-78°$ C. The gas composition, after removing acidic components from the collected product, was analyzed by gas chromatography and by $^{19}F$ NMR. The results are shown in Table 6-1.

EXAMPLE 6-2

The fluorination reaction and the analysis of the reaction products were conducted in the same manner as in Example 6 1 except that the catalyst prepared in Preparation Example 2 was used. The results are shown in Table 6-1.

EXAMPLE 6-3

The fluorination reaction and the analysis of the reaction products were conducted in the same manner as in Example 6-1 except that the catalyst prepared in Preparation Example 3 by using $Ba(NO_3)_2$ was used. The results are shown in Table 6-1.

TABLE 6-1

| Example No. | 6-1 | 6-2 | 6-3 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 82 | 67 | 52 |
| Selectivity (%) | | | |
| $CF_3CF_2CCl_2F$ | 24 | 32 | 38 |
| $CF_3CF_2CClF_2$ | 67 | 61 | 55 |
| Others | 9 | 7 | 7 |

EXAMPLE 6-4

The fluorination reaction and the analysis reaction products were conducted in the same manner as in Example 6-1 except that the catalyst prepared in Preparation Example 4 by using $Sr(NO_3)_2$ was used. The results are shown in Table 6-2.

EXAMPLE 6-5

The fluorination reaction and the analysis of the reaction products were conducted in the same manner as in Example 6-1 except that the catalyst prepared in Preparation Example 5 by using $Ca(NO_3)_2.4H_2O$ was used. The results are shown in Table 6-2.

EXAMPLE 6-6

The fluorination reaction and the analysis of the reaction products were conducted in the same manner as in Example 6-1 except that the catalyst prepared in Preparation Example 6 by using $Mn(NO_3)_2.4H_2O$ was used. The results are shown in Table 6-2.

TABLE 6-2

| Example No. | 6-4 | 6-5 | 6-6 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 44 | 50 | 70 |
| Selectivity (%) | | | |
| $CF_3CF_2CCl_2F$ | 34 | 40 | 29 |
| $CF_3CF_2CClF_2$ | 58 | 50 | 64 |
| Others | 8 | 10 | 7 |

EXAMPLE 6-7

The fluorination reaction and the analysis of the reaction products were conducted in the same manner as in Example 6-1 except that the catalyst prepared in Preparation Example 7 was used. The results are shown in Table 6-3.

EXAMPLE 6-8

The fluorination reaction and the analysis of the reaction products were conducted in the same manner as in Example 6-1 except that the catalyst prepared in Preparation Example 8 was used. The results are shown in Table 6-3.

EXAMPLE 6-9

The fluorination reaction and the analysis of the reaction products were conducted in the same manner as in Example 6-1 except that the catalyst prepared in Preparation Example 9 was used. The results are shown in Table 6-3.

TABLE 6-3

| Example No. | 6-7 | 6-8 | 6-9 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 38 | 41 | 37 |
| Selectivity (%) | | | |
| $CF_3CF_2CCl_2F$ | 44 | 48 | 46 |
| $CF_3CF_2CClF_2$ | 47 | 45 | 50 |
| Others | 9 | 7 | 4 |

EXAMPLE 6-10

The fluorination reaction and the analysis of the reaction products were conducted in the same manner as in Example 6-1 except that the catalyst prepared in Preparation Example 10 was used. The results are shown in Table 6-4.

EXAMPLE 6-11

The fluorination reaction and the analysis of the reaction products were conducted in the same manner as in Example 6-1 except that the catalyst prepared in Preparation Example 11 was used. The results are shown in Table 6-4.

EXAMPLE 6-12

The fluorination reaction and the analysis of the reaction products were conducted in the same manner as in Example 6-1 except that the catalyst prepared in Preparation Example 12 was used. The results are shown in Table 6-4.

TABLE 6-4

| Example No. | 6-10 | 6-11 | 6-12 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 38 | 41 | 37 |
| Selectivity (%) | | | |
| $CF_3CF_2CCl_2F$ | 44 | 48 | 46 |
| $CF_3CF_2CClF_2$ | 47 | 45 | 50 |
| Others | 9 | 7 | 4 |

EXAMPLE 6-13

The fluorination reaction and the analysis of the reaction products were conducted in the same manner as in Example 6-1 except that the catalyst prepared in Preparation Example 13 was used. The results are shown in Table 6-5.

EXAMPLE 6-14

The fluorination reaction and the analysis of the reaction products were conducted in the same manner as in Example 6-1 except that the catalyst prepared in Preparation Example 14 was used. The results are shown in Table 6-5.

TABLE 6-5

| Example No. | 6-13 | 6-14 |
|---|---|---|
| Reaction temp. (°C.) | 300 | 300 |
| Ratio of HF/starting material (molar ratio) | 3 | 3 |
| Contact time (sec) | 20 | 20 |
| Conversion (%) | 38 | 41 |
| Selectivity (%) | | |
| $CF_3CF_2CCl_2F$ | 44 | 48 |
| $CF_3CF_2CClF_2$ | 47 | 45 |
| Others | 9 | 7 |

EXAMPLE 6-15

The fluorination reaction and the analysis of the reaction products were conducted in the same manner as in Example 6-1 except that 2,2-difluoro-hexachloropropane was used. The results are shown in Table 6-6.

EXAMPLE 6-16

The fluorination reaction and the analysis of the reaction products were conducted in the same manner as in Example 6-1 except that 1,1,1,3,3-pentachlorotrifluoropropane was used. The results are shown in Table 6-6.

EXAMPLE 6-17

The fluorination reaction and the analysis of the reaction products were conducted in the same manner as in Example 6-1 except that 1,1,3,3-tetrachlorotetrafluoropropane was used. The results are shown in Table 6-6.

TABLE 6-6

| Example No. | 6-15 | 6-16 | 6-17 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 68 | 72 | 87 |
| Selectivity (%) | | | |
| $CCl_3CF_2CClF_2$ | 17 | 6 | |
| $CCl_2FCF_2CCl_2F$ | 6 | 14 | |
| $CCl_3CF_2CF_3$ | | 8 | |
| $CCl_2FCF_2CClF_2$ | 37 | 24 | 24 |

TABLE 6-6-continued

| Example No. | 6-15 | 6-16 | 6-17 |
|---|---|---|---|
| CCl$_2$FCF$_2$CF$_3$ | 10 | 7 | 15 |
| CClF$_2$CF$_2$CClF$_2$ | 23 | 33 | 54 |
| Others | 7 | 8 | 7 |

EXAMPLE 6-18

The fluorination reaction and the analysis of the reaction products were conducted in the same manner as in Example 6-1 except that 1,1,1,3-tetrachlorotetrafluoropropane was used. The results are shown in Table 6-7.

EXAMPLE 6-19

The fluorination reaction and the analysis of the reaction products were conducted in the same manner as in Example 6-1 except that 1,1,3-trichloropentafluoropropane was used. The results are shown in Table 6-7.

EXAMPLE 6-20

The fluorination reaction and the analysis of the reaction products were conducted in the same manner as in Example 6-1 except that 1,1,1-trichloropentafluoropropane was used. The results are shown in Table 6-7.

TABLE 6-7

| Example No. | 6-18 | 6-19 | 6-20 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 84 | 84 | 89 |
| Selectivity (%) | | | |
| CCl$_3$CF$_2$CF$_3$ | 11 | | |
| CCl$_2$FCF$_2$CClF$_2$ | 19 | | |
| CCl$_2$FCF$_2$CF$_3$ | 13 | 17 | 24 |
| CClF$_2$CF$_2$CClF$_2$ | 42 | 62 | |
| CClF$_2$CF$_2$CF$_3$ | 6 | 14 | 67 |
| Others | 9 | 7 | 9 |

EXAMPLE 6-21

The fluorination reaction and the analysis of the reaction products were conducted in the same manner as in Example 6-1 except that 1,3-dichloro-hexafluoropropane was used. The results are shown in Table 6-8.

EXAMPLE 6-22

The fluorination reaction and the analysis of the reaction products were conducted in the same manner as in Example 6-1 except that 1,1-dichloro-hexafluoropropane was used. The results are shown in Table 6-8.

EXAMPLE 6-23

The fluorination reaction and the analysis of the reaction products were conducted in the same manner as in Example 6-1 except that 1-chloro-heptafluoropropane was used. The results are shown in Table 6-8.

TABLE 6-8

| Example No. | 6-21 | 6-22 | 6-23 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 71 | 75 | 70 |
| Selectivity (%) | | | |
| CClF$_2$CF$_2$CF$_3$ | 81 | 85 | |
| CF$_3$CF$_2$CF$_3$ | 8 | 12 | 93 |
| Others | 11 | 3 | 7 |

EXAMPLE 7-1

An Inconnel 600 U-shaped reaction tube having an inner diameter of 2.54 cm and a length of 100 cm packed with 200 ml of fluorination catalyst prepared in the same manner as in Preparation Example 1, was used as a fluorination reactor. To the reactor kept at a temperature of 300° C., gasified 1,1,3-trichloro-2,2,3,3-tetrafluoropropane (R-224ca), oxygen and hydrogen fluoride were fed in at a rate of 50 ml/minutes, 2 ml/minutes and 100 ml/minuts, respectively and reacted. The reaction products were collected in a trap at −78° C. The gas composition after removing acidic components from the collected product, was analyzed by gas chromatography and by $^{19}$F-NMR. The results are shown in Table 7-1.

EXAMPLE 7-2

The fluorination reaction and the analysis of the reaction products were conducted in the same manner as in Example 7-1 except that the catalyst prepared in Preparation Example 2 was used. The results are shown in Table 7-1.

EXAMPLE 7-3

The fluorination reaction and the analysis of the reaction products were conducted in the same manner as in Example 7-1 except that the catalyst prepared in Preparation Example 3 by using Ba(NO$_3$)$_2$ was used. The results are shown in Table 7-1.

EXAMPLE 7-4

The fluorination reaction and the analysis of the reaction products were conducted in the same manner as in Example 7-1 except that the catalyst prepared in Preparation Example 4 by using Sr(NO$_3$)$_2$ was used. The results are shown in Table 7-1.

TABLE 7-1

| Example No. | 7-1 | 7-2 | 7-3 | 7-4 |
|---|---|---|---|---|
| Reaction temp. (°C.) | 300 | 300 | 300 | 300 |
| Ratio of HF/starting material (molar ratio) | 3 | 3 | 3 | 3 |
| Contact time (sec) | 20 | 20 | 20 | 20 |
| Conversion (%) | 80 | 70 | 62 | 58 |
| Selectivity (%) | | | | |
| CClF$_2$CF$_2$CHClF | 85 | 70 | 57 | 65 |
| CF$_3$CF$_2$CHCl$_2$ | 5 | 24 | 35 | 29 |
| CF$_3$C$_2$CHClF | 3 | 1 | 1 | 0 |
| CClF$_2$CF$_2$CHF$_2$ | 2 | 3 | 2 | 1 |
| Others | 5 | 2 | 5 | 5 |

EXAMPLE 7-5

The fluorination reaction and the analysis of the reaction products were conducted in the same manner as in Example 7-1 except that the catalyst prepared in Preparation Example 5 by using Ca(NO$_3$)$_2$.4H$_2$O was used. The results are shown in Table 7-2.

EXAMPLE 7-6

The fluorination reaction and the analysis of the reaction products were conducted in the same manner as in Example 7-1 except that the catalyst prepared in Preparation Example 6 by using $Mn(NO_3)_2 \cdot 4H_2O$ was used. The results are shown in Table 7-2.

EXAMPLE 7-7

The fluorination reaction and the analysis of the reaction products were conducted in the same manner as in Example 7-1 except that the catalyst prepared in Preparation Example 7 was used. The results are shown in Table 7-2.

EXAMPLE 7-8

The fluorination reaction and the analysis of the reaction products were conducted in the same manner as in Example 7-1 except that the catalyst prepared in Preparation Example 8 was used. The results are shown in Table 7-2.

TABLE 7-2

| Example No. | 7-5 | 7-6 | 7-7 | 7-8 |
|---|---|---|---|---|
| Reaction temp. (°C.) | 300 | 300 | 300 | 300 |
| Ratio of HF/starting material (molar ratio) | 3 | 3 | 3 | 3 |
| Contact time (sec) | 20 | 20 | 20 | 20 |
| Conversion (%) | 57 | 72 | 51 | 54 |
| Selectivity (%) | | | | |
| $CClF_2CF_2CHClF$ | 61 | 71 | 68 | 70 |
| $CF_3CF_2CHCl_2$ | 34 | 21 | 27 | 23 |
| $CF_3CF_2CHClF$ | 0 | 2 | 1 | 1 |
| $CClF_2CF_2CHF_2$ | 1 | 3 | 2 | 2 |
| Others | 4 | 3 | 2 | 4 |

EXAMPLE 7-9

The fluorination reaction and the analysis of the reaction products were conducted in the same manner as in Example 7-1 except that the catalyst prepared in Preparation Example 9 was used. The results are shown in Table 7-3.

EXAMPLE 7-10

The fluorination reaction and the analysis of the reaction products were conducted in the same manner as in Example 7-1 except that the catalyst prepared in Preparation Example 10 was used. The results are shown in Table 7-3.

EXAMPLE 7-11

The fluorination reaction and the analysis of the reaction products were conducted in the same manner as in Example 7-1 except that the catalyst prepared in Preparation Example 11 was used. The results are shown in Table 7-3.

EXAMPLE 7-12

The fluorination reaction and the analysis of the reaction products were conducted in the same manner as in Example 7-1 except that the catalyst prepared in Preparation Example 12 was used. The results are shown in Table 7-3.

TABLE 7-3

| Example No. | 7-9 | 7-10 | 7-11 | 7-12 |
|---|---|---|---|---|
| Reaction temp. (°C.) | 300 | 300 | 300 | 300 |
| Ratio of HF/starting material (molar ratio) | 3 | 3 | 3 | 3 |
| Contact time (sec) | 20 | 20 | 20 | 20 |
| Conversion (%) | 50 | 47 | 50 | 53 |
| Selectivity (%) | | | | |
| $CClF_2CF_2CHClF$ | 67 | 63 | 63 | 60 |
| $CF_3CF_2CHCl_2$ | 21 | 29 | 26 | 34 |
| $CF_3CF_2CHClF$ | 2 | 1 | 2 | 1 |
| $CClF_2CF_2CHF_2$ | 3 | 1 | 3 | 3 |
| Others | 7 | 6 | 6 | 2 |

EXAMPLE 7-13

The fluorination reaction and the analysis of the reaction products were conducted in the same manner as in Example 7-1 except that the catalyst prepared in Preparation Example 13 was used. The results are shown in Table 7-4.

EXAMPLE 7-14

The fluorination reaction and the analysis of the reaction products were conducted in the same manner as in Example 7-1 except that the catalyst prepared in Preparation Example 14 was used. The results are shown in Table 7-4.

TABLE 7-4

| Example No. | 7-13 | 7-14 |
|---|---|---|
| Reaction temp. (°C.) | 300 | 300 |
| Ratio of HF/starting material (molar ratio) | 3 | 3 |
| Contact time (sec) | 20 | 20 |
| Conversion (%) | 41 | 46 |
| Selectivity (%) | | |
| $CClF_2CF_2CHClF$ | 66 | 62 |
| $CF_3CF_2CHCl_2$ | 30 | 28 |
| $CF_3CF_2CHClF$ | 0 | 1 |
| $CClF_2CF_2CHF_2$ | 1 | 1 |
| Others | 3 | 8 |

EXAMPLE 7-15

The fluorination reaction and the analysis of the reaction products were conducted in the same manner as in Example 7-1 except that 1,1,1,3,3-pentachloro-2,2-difluoropropane was used. The results are shown in Table 7-5.

EXAMPLE 7-16

The fluorination reaction and the analysis of the reaction products were conducted in the same manner as in Example 7-1 except that 1,1,3,3-tetrachloro-1,2,2-trifluoropropane was used. The results are shown in Table 7-5.

EXAMPLE 7-17

The fluorination reaction and the analysis of the reaction products were conducted in the same manner as in Example 7-1 except that 1,1,1,3-tetrachloro-2,2,3-trifluoropropane was used. The results are shown in Table 7-5.

EXAMPLE 7-18

The fluorination reaction and the analysis of the reaction products were conducted in the same manner as in Example 7-1 except that 1,1,3-trichloro-2,2,3,3-tetrafluoropropane was used. The results are shown in Table 7-5.

EXAMPLE 7-19

The fluorination reaction and the analysis of the reaction products were conducted in the same manner as in Example 7-1 except that 1,1,3-trichloro-1,2,2,3-tetrafluoropropane was used. The results are shown in Table 7-5.

TABLE 7-5

| Example No. | 7-15 | 7-16 | 7-17 | 7-18 | 7-19 |
|---|---|---|---|---|---|
| Reaction temp. (°C.) | 300 | 300 | 300 | 300 | 300 |
| Ratio of HF/starting material (molar ratio) | 3 | 3 | 3 | 3 | 3 |
| Contact time (sec) | 20 | 20 | 20 | 20 | 20 |
| Conversion (%) | 74 | 73 | 79 | 75 | 80 |
| Selectivity (%) | | | | | |
| $CCl_2FCF_2CHClF$ | 6 | 9 | 10 | — | — |
| $CClF_2CF_2CHCl_2$ | 24 | 24 | — | — | — |
| $CClF_2CF_2CHClF$ | 53 | 50 | 54 | 68 | 85 |
| $CF_3CF_2CHCl_2$ | 5 | 7 | — | — | 5 |
| $CCl_2FCF_2CHF_2$ | — | — | 7 | — | — |
| $CClF_2CF_2CHF_2$ | 8 | 6 | 20 | 12 | 2 |
| $CF_3CF_2CHClF$ | 2 | 1 | 4 | 10 | 3 |
| Others | 2 | 3 | 5 | 5 | 5 |

EXAMPLE 7-20

The fluorination reaction and the analysis of the reaction products were conducted in the same manner as in Example 7-1 except that 1,1,1-trichloro-2,2,3,3-tetrafluoropropane was used. The results are shown in Table 7-6.

EXAMPLE 7-21

The fluorination reaction and the analysis of the reaction products were conducted in the same manner as in Example 7-1 except that 1,1-dichloro-2,2,3,3,3-pentafluoropropane was used. The results are shown in Table 7-6.

EXAMPLE 7-22

The fluorination reaction and the analysis of the reaction products were conducted in the same manner as in Example 7-1 except that 1,3-dichloro-1,1,2,2,3-pentafluoropropane was used. The results are shown in Table 7-6.

EXAMPLE 7-23

The fluorination reaction and the analysis of the reaction products were conducted in the same manner as in Example 7-1 except that 1,1-dichloro-1,2,2,3,3-pentafluoropropane was used. The results are shown in Table 7-6.

TABLE 7-6

| Example No. | 7-20 | 7-21 | 7-22 | 7-23 |
|---|---|---|---|---|
| Reaction temp. (°C.) | 300 | 300 | 300 | 300 |
| Ratio of HF/starting material (molar ratio) | 3 | 3 | 3 | 3 |
| Contact time (sec) | 20 | 20 | 20 | 20 |
| Conversion (%) | 72 | 83 | 80 | 81 |
| Selectivity (%) | | | | |
| $CCl_2FCF_2CHF_2$ | 12 | — | — | — |
| $CClF_2CF_2CHF_2$ | 71 | — | 57 | 74 |
| $CF_3CF_2CHClF$ | — | 78 | 32 | — |
| $CF_3CF_2CHF_2$ | 8 | 15 | 7 | 23 |
| Others | 9 | 7 | 4 | 3 |

EXAMPLE 7-24

The fluorination reaction and the analysis of the reaction products were conducted in the same manner as in Example 7-1 except that 1-chloro-1,2,2,3,3,3-hexafluoropropane was used. The results are shown in Table 7-7.

EXAMPLE 7-25

The fluorination reaction and the analysis of the reaction products were conducted in the same manner as in Example 7-1 except that 1-chloro-1,1,2,2,3,3-hexafluoropropane was used. The results are shown in Table 7-7.

TABLE 7-7

| Example No. | 7-24 | 7-25 |
|---|---|---|
| Reaction temp. (°C.) | 300 | 300 |
| Ratio of HF/starting material (molar ratio) | 3 | 3 |
| Contact time (sec) | 20 | 20 |
| Conversion (%) | 83 | 77 |
| Selectivity (%) | | |
| $CF_3CF_2CHF_2$ | 88 | 86 |
| Others | 12 | 14 |

EXAMPLE 8-1

An Inconnel 600 U-shaped reaction tube having an inner diameter of 2.54 cm and a length of 100 cm packed with 200 ml of fluorination catalyst prepared in the same manner as in Preparation Example 1, was used as a fluorination reactor. To the reactor kept at a temperature of 350° C., gasified 1,3-dichloro-1,1,2,2-tetrafluoropropane, oxygen and hydrogen fluoride were fed in at a rate of 50 ml/minutes, 2 ml/minutes and 100 ml/minutes, respectively and reacted. The reaction products were collected in a trap cooled at −78° C. The gas composition, after removing acidic components from the collected product, was analyzed by gas chromatography or and $^{19}F$-NMR. The results are shown in Table 8-1.

EXAMPLE 8-2

The fluorination reaction and the analysis of the reaction products were conducted in the same manner as in Example 8-1 except that the catalyst prepared in Preparation Example 2 was used. The results are shown in Table 8-1.

EXAMPLE 8-3

The fluorination reaction and the analysis of the reaction products were conducted in the same manner as in Example 8-1 except that the catalyst prepared in Preparation Example 3 by using $Ba(NO_3)_2$ was used. The results are shown in Table 8-1.

TABLE 8-1

| Example No. | 8-1 | 8-2 | 8-3 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 85 | 72 | 64 |
| Selectivity (%) | | | |
| $CClF_2CF_2CH_2F$ | 70 | 55 | 60 |
| $CF_3CF_2CH_2Cl$ | 23 | 47 | 33 |
| Others | 7 | 8 | 7 |

EXAMPLE 8-4

The fluorination reaction and the analysis of the reaction products were conducted in the same manner as in Example 8-1 except that the catalyst prepared in Preparation Example 4 by using $Sr(NO_3)_2$ was used. The results are shown in Table 8-2.

EXAMPLE 8-5

The fluorination reaction and the analysis of the reaction products were conducted in the same manner as in Example 8-1 except that the catalyst prepared in Preparation Example 5 by using $Ca(NO_3)_2 \cdot 4H_2O$ was used. The results are shown in Table 8-2.

EXAMPLE 8-6

The fluorination reaction and the analysis of the reaction products were conducted in the same manner as in Example 8-1 except that the catalyst prepared in Preparation Example 6 by using $Mn(NO_3)_2 \cdot 4H_2O$ was used. The results are shown in Table 8-2.

TABLE 8-2

| Example No. | 8-4 | 8-5 | 8-6 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 61 | 63 | 76 |
| Selectivity (%) | | | |
| $CClF_2CF_2CH_2F$ | 57 | 53 | 58 |
| $CF_3CF_2CH_2Cl$ | 36 | 41 | 36 |
| Others | 7 | 6 | 6 |

EXAMPLE 8-7

The fluorination reaction and the analysis of the reaction products were conducted in the same manner as in Example 8-1 except that the catalyst prepared in Preparation Example 7 was used. The results are shown in Table 8-3.

EXAMPLE 8-8

The fluorination reaction and the analysis of the reaction products were conducted in the same manner as in Example 8-1 except that the catalyst prepared in Preparation Example 8 was used. The results are shown in Table 8-3.

EXAMPLE 8-9

The fluorination reaction and the analysis of the reaction products were conducted in the same manner as in Example 8-1 except that the catalyst prepared in Preparation Example 9 was used. The results are shown in Table 8-3.

TABLE 8-3

| Example No. | 8-7 | 8-8 | 8-9 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 38 | 42 | 40 |
| Selectivity (%) | | | |
| $CClF_2CF_2CH_2F$ | 45 | 52 | 44 |
| $CF_3CF_2CH_2Cl$ | 49 | 40 | 48 |
| Others | 6 | 8 | 8 |

EXAMPLE 8-10

The fluorination reaction and the analysis of the reaction products were conducted in the same manner as in Example 8-1 except that the catalyst prepared in Preparation Example 10 was used. The results are shown in Table 8-4.

EXAMPLE 8-11

The fluorination reaction and the analysis of the reaction products were conducted in the same manner as in Example 8-1 except that the catalyst prepared in Preparation Example 11 was used. The results are shown in Table 8-4.

EXAMPLE 8-12

The fluorination reaction and the analysis of the reaction products were conducted in the same manner as in Example 8-1 except that the catalyst prepared in Preparation Example 12 was used. The results are shown in Table 8-4.

TABLE 8-4

| Example No. | 8-10 | 8-11 | 8-12 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 67 | 41 | 42 |
| Selectivity (%) | | | |
| $CClF_2CF_2CH_2F$ | 50 | 46 | 54 |
| $CF_3CF_2CH_2Cl$ | 43 | 46 | 41 |
| Others | 7 | 8 | 5 |

EXAMPLE 8-13

The fluorination reaction and the analysis of the reaction products were conducted in the same manner as in Example 8-1 except that the catalyst prepared in Preparation Example 13 was used. The results are shown in Table 8-5.

EXAMPLE 8-14

The fluorination reaction and the analysis of the reaction products were conducted in the same manner as in Example 8-1 except that the catalyst prepared in Preparation Example 14 was used. The results are shown in Table 8-5.

TABLE 8-5

| Example No. | 8-13 | 8-14 |
|---|---|---|
| Reaction temp. (°C.) | 300 | 300 |
| Ratio of HF/starting material (molar ratio) | 3 | 3 |
| Contact time (sec) | 20 | 20 |
| Conversion (%) | 62 | 60 |
| Selectivity (%) | | |
| $CClF_2CF_2CH_2F$ | 48 | 47 |
| $CF_3CF_2CH_2Cl$ | 44 | 45 |
| Others | 8 | 8 |

EXAMPLE 8-15

The fluorination reaction and the analysis of the reaction products were conducted in the same manner as in Example 8-1 except that 1,1,3,3-tetrachloro-2,2-difluoropropane was used. The results are shown in Table 8-6.

EXAMPLE 8-16

The fluorination reaction and the analysis of the reaction products were conducted in the same manner as in Example 8-1 except that 1,1,1,3-tetrachloro-2,2-difluoropropane was used. The results are shown in Table 8-6.

EXAMPLE 8-17

The fluorination reaction and the analysis of the reaction products were conducted in the same manner as in Example 8-1 except that 1,1,3-trichloro-2,2,3-trifluoropropane was used. The results are shown in Table 8-6.

TABLE 8-6

| Example No. | 8-15 | 8-16 | 8-17 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 74 | 70 | 81 |
| Selectivity (%) | | | |
| $CClF_2CF_2CH_2F$ | 50 | 46 | 54 |
| $CF_3CF_2CH_2Cl$ | 43 | 46 | 41 |
| Others | 7 | 8 | 5 |

EXAMPLE 8-18

The fluorination reaction and the analysis of the reaction products were conducted in the same manner as in Example 8-1 except that 1,1,3-trichloro-1,2,2-trifluoropropane was used. The results are shown in Table 8-7.

EXAMPLE 8-19

The fluorination reaction and the analysis of the reaction products were conducted in the same manner as in Example 8-1 except that 1,1,1-trichloro-2,2,3-trifluoropropane was used. The results are shown in Table 8-7.

EXAMPLE 8-20

The fluorination reaction and the analysis of the reaction products were conducted in the same manner as in Example 8-1 except that 1,1-dichloro-1,2,2,3-tetrafluoropropane was used. The results are shown in Table 8-7.

TABLE 8-7

| Example No. | 8-18 | 8-19 | 8-20 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 77 | 83 | 76 |
| Selectivity (%) | | | |
| $CCl_2FCF_2CH_2F$ | 10 | 31 | |
| $CClF_2CF_2CH_2Cl$ | 58 | | |
| $CHClFCF_2CHF_2$ | | | 72 |
| $CClF_2CF_2CH_2F$ | 20 | 64 | |
| $CF_3CF_2CH_2Cl$ | 4 | | |
| $CHF_2CF_2CHF_2$ | | 1 | 20 |
| Others | 8 | 4 | 8 |

EXAMPLE 8-21

The fluorination reaction and the analysis of the reaction products were conducted in the same manner as in Example 8-1 except that 1,1-dichloro-2,2,3,3-tetrafluoropropane was used. The results are shown in Table 8-8.

EXAMPLE 8-22

The fluorination reaction and the analysis of the reaction products were conducted in the same manner as in Example 8-1 except that 1,3-dichloro-1,1,2,2-tetrafluoropropane was used. The results are shown in Table 8-8.

EXAMPLE 8-23

The fluorination reaction and the analysis of the reaction products were conducted in the same manner as in Example 8-1 except that 1,1-dichloro-1,2,2,3-tetrafluoropropane was used. The results are shown in Table 8-8.

TABLE 8-8

| Example No. | 8-21 | 8-22 | 8-23 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 64 | 69 | 72 |
| Selectivity (%) | | | |
| $CHClFCF_2CHF_2$ | 68 | | |
| $CClF_2CF_3CH_2F$ | | 70 | 81 |
| $CF_3CF_2CH_2Cl$ | | 18 | |
| $CHF_2CF_2CHF_2$ | 28 | | |
| $CF_3CF_2CH_2F$ | | 5 | 12 |
| Others | 4 | 7 | 7 |

EXAMPLE 8-24

The fluorination reaction and the analysis of the reaction products were conducted in the same manner as in Example 8-1 except that 3-chloro-1,1,2,2,3-pentafluoropropane was used. The results are shown in Table 8-9.

EXAMPLE 8-25

The fluorination reaction and the analysis of the reaction products were conducted in the same manner as in Example 8-1 except that 3-chloro-1,1,1,1,2,2-pentafluoropropane was used. The results are shown in Table 8-9.

EXAMPLE 8-26

The fluorination reaction and the analysis of the reaction products were conducted in the same manner as in Example 8-1 except that 1-chloro-1,1,2,2,3-pentafluoropropane was used. The results are shown in Table 8-9.

TABLE 8-9

| Example No. | 8-24 | 8-25 | 8-26 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 63 | 60 | 64 |
| Selectivity (%) | | | |
| $CHF_2CF_2CHF_2$ | 90 | | |
| $CF_3CF_2CH_2F$ | | 94 | 92 |
| Others | 10 | 6 | 8 |

EXAMPLE 9-1

An Inconnel 600 U-shaped reaction tube having an inner diameter of 2.54 cm and a length of 100 cm packed with 200 ml of fluorination catalyst prepared in the same manner as in Preparation Example 1, was used as a fluorination reactor. To the reactor kept at a temperature of 350° C., gasified 1,3-dichloro-1,1,2,2-tetrafluoropropane, oxygen and hydrogen fluoride were fed in at a rate of 50 ml/minutes, 2 ml/minutes and 100 ml/minutes, respectively and reacted. The reaction products were collected in a trap cooled at −78° C. The gas composition, after removing acidic components from the collected product, was analyzed by gas chromatography and by 19F-NMR. The results are shown in Table 9-1.

EXAMPLE 9-2

The fluorination reaction and the analysis of the reaction products were conducted in the same manner as in Example 9-1 except that the catalyst prepared in Preparation Example 2 was used. The results are shown in Table 9-1.

EXAMPLE 9-3

The fluorination reaction and the analysis of the reaction products were conducted in the same manner as in Example 9-1 except that the catalyst prepared in Preparation Example 3 by using $Ba(NO_3)_2$ was used. The results are shown in Table 9-1.

TABLE 9-1

| Example No. | 9-1 | 9-2 | 9-3 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 83 | 70 | 61 |
| Selectivity (%) | | | |
| $CHClFCF_2CH_2F$ | 55 | 67 | 70 |
| $CHF_2CF_2CH_2F$ | 41 | 27 | 23 |
| Others | 4 | 6 | 7 |

EXAMPLE 9-4

The fluorination reaction and the analysis of the reaction products were conducted in the same manner as in Example 9-1 except that the catalyst prepared in Preparation Example 4 by using $Sr(NO_3)_2$ was used. The results are shown in Table 9-2.

EXAMPLE 9-5

The fluorination reaction and the analysis of the reaction products were conducted in the same manner as in Example 9-1 except that the catalyst prepared in Preparation Example 5 by using $Ca(NO_3)_2.4H_2O$ was used. The results are shown in Table 9-2.

EXAMPLE 9-6

The fluorination reaction and the analysis of the reaction products were conducted in the same manner as in Example 9-1 except that the catalyst prepared in Preparation Example 6 by using $Mn(NO_3)_2.4H_2O$ was used. The results are shown in Table 9-2.

TABLE 9-2

| Example No. | 9-4 | 9-5 | 9-6 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 63 | 55 | 72 |
| Selectivity (%) | | | |
| $CHClFCF_2CH_2F$ | 66 | 71 | 59 |
| $CHF_2CF_2CH_2F$ | 30 | 22 | 35 |
| Others | 4 | 7 | 6 |

EXAMPLE 9-7

The fluorination reaction and the analysis of the reaction products were conducted in the same manner as in Example 9-1 except that the catalyst prepared in Preparation Example 7 was used. The results are shown in Table 9-3.

EXAMPLE 9-8

The fluorination reaction and the analysis of the reaction products were conducted in the same manner as in Example 9-1 except that the catalyst prepared in Preparation Example 8 was used. The results are shown in Table 9-3.

EXAMPLE 9-9

The fluorination reaction and the analysis of the reaction products were conducted in the same manner as in Example 9-1 except that the catalyst prepared in Preparation Example 9 was used. The results are shown in Table 9-3.

TABLE 9-3

| Example No. | 9-7 | 9-8 | 9-9 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 42 | 44 | 40 |
| Selectivity (%) | | | |
| $CHClFCF_2CH_2F$ | 73 | 68 | 76 |
| $CHF_2CF_2CH_2F$ | 20 | 25 | 18 |
| Others | 7 | 7 | 6 |

EXAMPLE 9-10

The fluorination reaction and the analysis of the reaction products were conducted in the same manner as in Example 9-1 except that the catalyst prepared in Preparation Example 10 was used. The results are shown in Table 9-4.

EXAMPLE 9-11

The fluorination reaction and the analysis of the reaction products were conducted in the same manner as in Example 9-1 except that the catalyst prepared in Preparation Example 11 was used. The results are shown in Table 9-4.

EXAMPLE 9-12

The fluorination reaction and the analysis of the reaction products were conducted in the same manner as in Example 9-1 except that the catalyst prepared in Preparation Example 12 was used. The results are shown in Table 9-4.

TABLE 9-4

| Example No. | 9-10 | 9-11 | 9-12 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 63 | 42 | 48 |
| Selectivity (%) | | | |
| $CHClFCF_2CH_2F$ | 65 | 72 | 74 |
| $CHF_2CF_2CH_2F$ | 30 | 21 | 21 |
| Others | 5 | 7 | 5 |

EXAMPLE 9-13

The fluorination reaction and the analysis of the reaction products were conducted in the same manner as in Example 9-1 except that the catalyst prepared in Preparation Example 13 was used. The results are shown in Table 9-5.

EXAMPLE 9-14

The fluorination reaction and the analysis of the reaction products were conducted in the same manner as in Example 9-1 except that the catalyst prepared in Preparation Example 14 was used. The results are shown in Table 9-5.

TABLE 9-5

| Example No. | 9-13 | 9-14 |
|---|---|---|
| Reaction temp. (°C.) | 300 | 300 |
| Ratio of HF/starting material (molar ratio) | 3 | 3 |
| Contact time (sec) | 20 | 20 |
| Conversion (%) | 63 | 42 |
| Selectivity (%) | | |
| CHClFCF$_2$CH$_2$F | 65 | 72 |
| CHF$_2$CF$_2$CH$_2$F | 30 | 21 |
| Others | 5 | 7 |

EXAMPLE 9-15

The fluorination reaction and the analysis of the reaction products were conducted in the same manner as in Example 9-1 except that 1,1,3-trichloro-2,2-difluoropropane was used. The results are shown in Table 9-6.

EXAMPLE 9-16

The fluorination reaction and the analysis of the reaction products were conducted in the same manner as in Example 9-1 except that 1,1,1-trichloro-2,2-difluoropropane was used. The results are shown in Table 9-6.

EXAMPLE 9-17

The fluorination reaction and the analysis of the reaction products were conducted in the same manner as in Example 9-1 except that 1,3-dichloro-1,2,2-trifluoropropane was used. The results are shown in Table 9-6.

EXAMPLE 9-18

The fluorination reaction and the analysis of the reaction products were conducted in the same manner as in Example 9-1 except that 1,1-dichloro-2,2,3-trifluoropropane was used. The results are shown in Table 9-6.

TABLE 9-6

| Example No. | 9-15 | 9-16 | 9-17 | 9-18 |
|---|---|---|---|---|
| Reaction temp. (°C.) | 300 | 300 | 300 | 300 |
| Ratio of HF/starting material (molar ratio) | 3 | 3 | 3 | 3 |
| Contact time (sec) | 20 | 20 | 20 | 20 |
| Conversion (%) | 84 | 77 | 80 | 68 |
| Selectivity (%) | | | | |
| CHClFCF$_2$CH$_2$Cl | 19 | | | |
| CHCl$_2$CF$_2$CH$_2$F | 22 | | | |
| CH$_3$CF$_2$CCl$_2$F | | 21 | | |
| CHClFCF$_2$CH$_2$F | 43 | | 53 | 55 |
| CHF$_2$CF$_2$CH$_2$Cl | 9 | | 29 | |
| CH$_3$CF$_2$CClF$_2$ | | 60 | | |
| CF$_3$CF$_2$CH$_3$ | | 12 | 10 | 41 |
| Others | 7 | 7 | 8 | 9 |

EXAMPLE 9-19

The fluorination reaction and the analysis of the reaction products were conducted in the same manner as in Example 9-1 except that 1,1-dichloro-1,2,2-trifluoropropane was used. The results are shown in Table 9-7.

EXAMPLE 9-20

The fluorination reaction and the analysis of the reaction products were conducted in the same manner as in Example 9-1 except that 3-chloro-1,1,2,2-tetrafluoropropane was used. The results are shown in Table 9-7.

EXAMPLE 9-21

The fluorination reaction and the analysis of the reaction products were conducted in the same manner as in Example 9-1 except that 1-chloro-1,2,2,3-tetrafluoropropane was used. The results are shown in Table 9-7.

EXAMPLE 9-22

The fluorination reaction and the analysis of the reaction products were conducted in the same manner as in Example 9-1 except that 1-chloro-1,1,2,2-tetrafluoropropane was used. The results are shown in Table 9-7.

TABLE 9-7

| Example No. | 9-19 | 9-20 | 9-21 | 9-22 |
|---|---|---|---|---|
| Reaction temp. (°C.) | 300 | 300 | 300 | 300 |
| Ratio of HF/starting material (molar ratio) | 3 | 3 | 3 | 3 |
| Contact time (sec) | 20 | 20 | 20 | 20 |
| Conversion (%) | 62 | 53 | 61 | 68 |
| Selectivity (%) | | | | |
| CHClFCF$_2$CH$_2$F | 87 | | | |
| CF$_3$CF$_2$CH$_3$ | | | | 92 |
| CHF$_2$CF$_2$CH$_2$F | 7 | 93 | 93 | |
| Others | 6 | 7 | 7 | 8 |

EXAMPLE 10-1

An Inconnel 600 U-shaped reaction tube having an inner diameter of 2.54 cm and a length of 100 cm packed with 200 ml of fluorination catalyst prepared in the same manner as in Preparation Example 1, was used as a fluorination reactor. To the reactor kept at a temperature of 350° C., gasified 1,3-dichloro-1,1,2,2-tetrafluoropropane, oxygen and hydrogen fluoride were fed in at a rate of 50 ml/minutes, 2 ml/minutes and 100 ml/minutes, respectively and reacted. The reaction products were collected in a trap cooled at −78° C. The gas composition, after removing acidic components from the collected product, was analyzed by gas chromatography or by $^{19}$F-NMR. The results are shown in Table 10-1.

EXAMPLE 10-2

The fluorination reaction and the analysis of the reaction products were conducted in the same manner as in Example 10-1 except that the catalyst prepared in Preparation Example 2 was used. The results are shown in Table 10-1.

EXAMPLE 10-3

The fluorination reaction and the analysis of the reaction products were conducted in the same manner as in Example 10-1 except that the catalyst prepared in Preparation Example 3 by using Ba(NO$_3$)$_2$ was used. The results are shown in Table 10-1.

TABLE 10-1

| Example No. | 10-1 | 10-2 | 10-3 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 80 | 74 | 68 |
| Selectivity (%) | | | |
| CHClFCF$_2$CH$_3$ | 82 | 80 | 85 |
| CHF$_2$CF$_2$CH$_3$ | 14 | 13 | 11 |

TABLE 10-1-continued

| Example No. | 10-1 | 10-2 | 10-3 |
|---|---|---|---|
| Others | 6 | 7 | 4 |

EXAMPLE 10-4

The fluorination reaction and the analysis of the reaction products were conducted in the same manner as in Example 10-1 except that the catalyst prepared in Preparation Example 4 by using $Sr(NO_3)_2$ was used. The results are shown in Table 10-2.

EXAMPLE 10-5

The fluorination reaction and the analysis of the reaction products were conducted in the same manner as in Example 10-1 except that the catalyst prepared in Preparation Example 5 by using $Ca(NO_3)_2 \cdot 4H_2O$ was used. The results are shown in Table 10-2.

EXAMPLE 10-6

The fluorination reaction and the analysis of the reaction products were conducted in the same manner as in Example 10-1 except that the catalyst prepared in Preparation Example 6 by using $Mn(NO_3)_2 \cdot 4H_2O$ was used. The results are shown in Table 10-2.

TABLE 10-2

| Example No. | 10-4 | 10-5 | 10-6 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 60 | 63 | 76 |
| Selectivity (%) | | | |
| $CHClFCF_2CH_3$ | 88 | 84 | 86 |
| $CHF_2CF_2CH_3$ | 7 | 8 | 9 |
| Others | 5 | 8 | 5 |

EXAMPLE 10-7

The fluorination reaction and the anal reaction products were conducted in the same manner as in Example 10-1 except that the catalyst prepared in Preparation Example 7 was used. The results are shown in Table 10-3.

EXAMPLE 10-8

The fluorination reaction and the analysis of the reaction products were conducted in the same manner as in Example 10-1 except that the catalyst prepared in Preparation Example 8 was used. The results are shown in Table 10-3.

EXAMPLE 10-9

The fluorination reaction and the analysis of the reaction products were conducted in the same manner as in Example 10-1 except that the catalyst prepared in Preparation Example 9 was used. The results are shown in Table 10-3.

TABLE 10-3

| Example No. | 10-7 | 10-8 | 10-9 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 35 | 40 | 36 |
| Selectivity (%) | | | |
| $CHClFCF_2CH_3$ | 90 | 93 | 92 |
| $CHF_2CF_2CH_3$ | 3 | 2 | |
| Others | 7 | 5 | 8 |

EXAMPLE 10-10

The fluorination reaction and the analysis of the reaction products were conducted in the same manner as in Example 10-1 except that the catalyst prepared in Preparation Example 10 was used. The results are shown in Table 10-4.

EXAMPLE 10-11

The fluorination reaction and the analysis of the reaction products were conducted in the same manner as in Example 10-1 except that the catalyst prepared in Preparation Example 11 was used. The results are shown in Table 10-4.

EXAMPLE 10-12

The fluorination reaction and the analysis of the reaction products were conducted in the same manner as in Example 10-1 except that the catalyst prepared in Preparation Example 12 was used. The results are shown in Table 10-4.

TABLE 10-5

| Example No. | 10-13 | 10-14 |
|---|---|---|
| Reaction temp. (°C.) | 300 | 300 |
| Ratio of HF/starting material (molar ratio) | 3 | 3 |
| Contact time (sec) | 20 | 20 |
| Conversion (%) | 65 | 61 |
| Selectivity (%) | | |
| $CHClFCF_2CH_3$ | 90 | 93 |
| $CHF_2CF_2CH_3$ | 2 | |
| Others | 8 | 7 |

EXAMPLE 10-15

The fluorination reaction and the analysis of the reaction products were conducted in the same manner as in Example 10-1 except that 1,3-dichloro-2,2-difluoropropane was used. The results are shown in Table 10-6.

EXAMPLE 10-16

The fluorination reaction and the analysis of the reaction products were conducted in the same manner as in Example 10-1 except that 1,1-dichloro-2,2-difluoropropane was used. The results are shown in Table 10-6.

EXAMPLE 10-17

The fluorination reaction and the analysis of the reaction products were conducted in the same manner as in Example 10-1 except that 1-chloro-2,2,3-trifluoropropane was used. The results are shown in Table 10-6.

EXAMPLE 10-18

The fluorination reaction and the analysis of the reaction products were conducted in the same manner as in Example 10-1 except that 1-chloro-1,2,2-trifluoropropane 5 was used. The results are shown in Table 10-6.

TABLE 10-6

| Example No. | 10-15 | 10-16 | 10-17 | 10-18 |
|---|---|---|---|---|
| Reaction temp. (°C.) | 300 | 300 | 300 | 300 |

TABLE 10-6-continued

| Example No. | 10-15 | 10-16 | 10-17 | 10-18 |
|---|---|---|---|---|
| Ratio of HF/starting material (molar ratio) | 3 | 3 | 3 | 3 |
| Contact time (sec) | 20 | 20 | 20 | 20 |
| Conversion (%) | 77 | 53 | 64 | 60 |
| Selectivity (%) | | | | |
| $CH_2FCF_2CH_2Cl$ | 58 | | | |
| $CH_3CF_2CHClF$ | | 80 | | |
| $CH_2FCF_2CH_2F$ | 34 | | 97 | |
| $CH_3CF_2CHF_2$ | | 14 | | 91 |
| Others | 8 | 6 | 3 | 9 |

EXAMPLE 11-1

Into a 1 l Hastelloy C autoclave, 50 g of 1,1,1,3,3,3-hexachloro-2,2-difluoropropane (R-212ca), 90 g of spray-dried potassium fluoride, 9 g of tetrabutylphosphonium bromide and 480 g of sulfolane, were charged, and the reaction was conducted at a temperature of 200° C. for 10 hours under vigorously stirring. After cooling, inorganic salts were removed by filtration, and the reaction products were analyzed by gas chromatography and by NMR. As the results, it was confirmed that 1,1,1,3,3,3-pentachloro-2,2,3-trifluoropropane (R-213ca), 1,1,3,3-tetrachloro-1,2,2,3-tetrafluoropropane (R-214ca), 1,1,1,3-tetrachloro-2,2,2,3-tetrafluoropropane (R-214cb), 1,1,3-trichloro-1,2,2,3,3-pentafluoropropane (R-215ca), 1,1,1-trichloro-2,2,3,3,3-pentafluoropropane (R-215cb), 1,3-dichloro-1,1,2,2,3,3-hexafluoropropane (R-216ca), 1,1-dichloro-1,2,2,3,3,3-hexafluoropropane (R-216cb), 1-chloro-1,1,2,2,2,3,3,3-heptafluoropropane (R-217ca) and octafluoropropane (R-218), were formed. The results are shown in Table 11-1.

TABLE 11-1

| Conversion of R-212ca | 99% |
|---|---|
| Selectivity for R-214ca | 4% |
| Selectivity for R-215ca | 13% |
| Selectivity for R-216ca | 24% |
| Selectivity for R-216cb | 20% |
| Selectivity for R-217ca | 14% |

EXAMPLE 11-2

The fluorination reaction and the analysis of the reaction products were conducted in the same manner as in Example 11-1 except that 1,1,1,3,3-pentachloro-2,2,3-trifluoropropane (R-213ca) was used as the starting material. The results are shown in Table 11-2.

TABLE 11-2

| Conversion of R-213ca | 99% |
|---|---|
| Selectivity for R-214ca | 2% |
| Selectivity for R-215ca | 6% |
| Selectivity for R-216ca | 24% |
| Selectivity for R-216cb | 20% |
| Selectivity for R-217ca | 27% |

EXAMPLE 11-3

The fluorination reaction and the analysis of the reaction products were conducted in the same manner as in Example 11-1 except that as the starting material, 50 g of 1,1,3,3-tetrachloro-1,2,2,3-tetrafluoropropane (R-214ca), 70 g of spray-dried potassium fluoride and 7 g of tetrabutylsulphonium bromide, were used. The results are shown in Table 11-3.

TABLE 11-3

| Conversion of R-214ca | 99% |
|---|---|
| Selectivity for R-215ca | 5% |
| Selectivity for R-216ca | 14% |
| Selectivity for R-216cb | 8% |
| Selectivity for R-217ca | 43% |
| Selectivity for R-218ca | 26% |

EXAMPLE 11-4

The fluorination reaction and the analysis of the reaction products were conducted in the same manner as in Example 11-1 except that as the starting material, 1,1,1,3-tetrachloro-2,2,3,3-tetrafluoropropane (R-214cb), was used. The results are shown in Table 11-4.

TABLE 11-4

| Conversion of R-214cb | 99% |
|---|---|
| Selectivity for R-215cb | 7% |
| Selectivity for R-216ca | 13% |
| Selectivity for R-216cb | 9% |
| Selectivity for R-217ca | 35% |
| Selectivity for R-218ca | 29% |

EXAMPLE 11-5

The fluorination reaction and the analysis of the reaction products were conducted in the same manner as in Example 11-1 except that as the starting materials, 50 g of 1,1,3 trichloro-1,2,2,3,3-pentafluoropropane (R-215ca), 55 g of spray-dried potassium fluoride and 6 g of tetrabutylphosphonium bromide, was used. The results are shown in Table 11-5.

TABLE 10-4

| Example No. | 10-10 | 10-11 | 10-12 |
|---|---|---|---|
| Reaction temp. (°C.) | 300 | 300 | 300 |
| Ratio of HF/starting material (molar ratio) | 3 | 3 | 3 |
| Contact time (sec) | 20 | 20 | 20 |
| Conversion (%) | 71 | 38 | 38 |
| Selectivity (%) | | | |
| $CHClFCF_2CH_3$ | 83 | 91 | 92 |
| $CHF_2CF_2CH_3$ | 9 | | |
| Others | 8 | 9 | 8 |

EXAMPLE 10-13

The fluorination reaction and the analysis of the reaction products were conducted in the same manner as in Example 10-1 except that the catalyst prepared in Preparation Example 13 was used. The results are shown in Table 10-5.

EXAMPLE 10-14

The fluorination reaction and the analysis of the reaction products were conducted in the same manner as in Example 10-1 except that the catalyst prepared in Preparation Example 14 was used. The results are shown in Table 10-5.

TABLE 11-5

| Conversion of R-215ca | 99% |
|---|---|
| Selectivity for R-216ca | 11% |
| Selectivity for R-216cb | 9% |
| Selectivity for R-217ca | 35% |
| Selectivity for R-218ca | 41% |

EXAMPLE 11-6

The fluorination reaction and the analysis of the reaction products were conducted in the same manner as in Example 11-5 except that as the starting material, 1,1,1-trichloro-2,2,3,3,3-pentafluoropropane (R-215cb), was used. The results are shown in Table 11-6.

TABLE 11-6

| Conversion of R-215cb | 99% |
| --- | --- |
| Selectivity for R-216cb | 17% |
| Selectivity for R-217ca | 40% |
| Selectivity for R-218ca | 37% |

EXAMPLE 11-7

The fluorination reaction and the analysis of the reaction products were conducted in the same manner as in Example 11-1 except that as the starting materials, 50 g of 1,3-dichloro-1,1,2,2,3,3-hexafluoropropane (R-216cb), 40 g of spray-dried potassium fluoride and 4 g of tetrabutylsulfonium bromide, were used. The results are shown in Table 11-7.

TABLE 11-7

| Conversion of R-216ca | 92% |
| --- | --- |
| Selectivity for R-217ca | 35% |
| Selectivity for R-218ca | 61% |

EXAMPLE 11-8

The fluorination reaction and the analysis of the reaction products were conducted in the same manner as in Example 11-7 except that as the starting material, 1,1-dichloro-1,2,2,3,3,3-hexafluoropropane (R-216cb), was used. The results are shown in Table 11-8.

TABLE 11-8

| Conversion of R-216cb | 94% |
| --- | --- |
| Selectivity for R-217ca | 33% |
| Selectivity for R-218ca | 63% |

EXAMPLE 11-9

The fluorination reaction and the analysis of the reaction products were conducted in the same manner as in Example 11-1 except that as the starting materials, 50 g of 1-chloro-1,1,2,2,3,3,3-heptafluoropropane (R-217ca), 55 g of cesium fluoride and 6 g of tetrabutylammonium bromide, were used and the reaction temperature was changed to 150° C. The results are shown in Table 11-9.

TABLE 11-9

| Conversion of R-217ca | 91% |
| --- | --- |
| Selectivity for R-218ca | 96% |

EXAMPLE 11-10

Into a 200 ml Hastelloy C autoclave, as the starting materials, 150 g of 1,1,1-trichloro-2,2,3,3,3-pentafluoropropane (R-215cb) and 60 g of antimony trifluoride, were charged, and the reaction was conducted at a temperature of 150° C. for 10 hours under vigorously stirring. After cooling, inorganic salts were removed by filtration; The crude reaction solution was washed with water and dried. Then, the reaction products were analyzed by gas chromatography and by NMR. The results are shown in Table 11-10.

TABLE 11-10

| Conversion of R-215cb | 22% |
| --- | --- |
| Selectivity for R-216cb | 70% |
| Selectivity for R-217ca | 19% |
| Selectivity for R-218ca | 7% |

EXAMPLE 11-11

Into a 200 ml Hastelloy C autoclave, as the starting material, 150 g of 1,1,1-trichloro-2,2,3,3,3-pentafluoropropane (R-215cb), 60 g of antimony trifluoride and 3 g of antimony trichloride, were charged, and the reaction was conducted at a temperature of 150° C. for 10 hours under vigorously stirring. After cooling, inorganic salts were removed by filtration. The crude reaction solution was washed with water and dried. Then, the reaction products were analyzed by gas chromatography and by NMR. The results are shown in Table 11-11.

TABLE 11-11

| Conversion of R-215cb | 30% |
| --- | --- |
| Selectivity for R-216cb | 65% |
| Selectivity for R-217ca | 29% |
| Selectivity for R-218ca | 4% |

EXAMPLE 11-12

Into a 200 ml Hastelloy C autoclave, as the starting material, 150 g of 1,1,1-trichloro-2,2,3,3,3-pentafluoropropane (R-215cb), 60 g of antimony trifluoride and 3 g of antimony pentafluoride, were charged, and the reaction was conducted at a temperature of 150° C. for 10 hours under vigorously stirring. After cooling, inorganic salts were removed by filtration. The crude reaction solution was washed with water and dried. Then, the reaction products were analyzed by gas chromatography and by NMR. The results are shown in Table 11-12.

TABLE 11-12

| Conversion of R-215cb | 31% |
| --- | --- |
| Selectivity for R-216cb | 65% |
| Selectivity for R-217ca | 25% |
| Selectivity for R-218ca | 7% |

EXAMPLE 11-13

Into a 200 ml Hastelloy C autoclave, 60 g of antimony trifluoride was added, and then 23 g of chlorine gas was introduced to prepare antimony dichloride trifluoride. The thin film of antimony dichloride trifluoride thereby formed was broken, and as the starting material, 150 g of 1,1,1-trichloro-2,2,3,3,3-pentafluoropropane (R-215cb) was charged. The reaction was conducted at a temperature of 150° C. for 10 hours under vigorously stirring. After cooling, inorganic salts were removed by filtration, and the crude reaction solution was washed and dried. Then, the reaction products were analyzed by gas chromatography and by NMR. The results are shown in Table 11-13.

TABLE 11-13

| Conversion of R-215cb | 34% |
| --- | --- |
| Selectivity for R-216cb | 65% |
| Selectivity for R-217ca | 26% |

TABLE 11-13-continued

| Conversion of R-215cb | 34% |
|---|---|
| Selectivity for R-218ca | 5% |

EXAMPLE 11-14

Into a 200 ml Hastelloy C autoclave, as the starting materials, 150 g of 1,1,1-trichloro-2,2,3,3,3-pentafluoropropane (R-215cb) and 80 g of antimony pentafluoride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 11-14.

TABLE 11-14

| Conversion of R-215cb | 38% |
|---|---|
| Selectivity for R-216cb | 67% |
| Selectivity for R-217ca | 22% |
| Selectivity for R-218ca | 6% |

EXAMPLE 12-1

Into a 1 l Hastelloy C autoclave, as the starting materials, 50 g of 1,1,1,3,3-pentachloro-2,2-difluoropropane (R-222ca), 87 g of spray-dried potassium fluoride, 9 g of tetrabutylsulfonium bromide and 480 g of sulfolane, were charged, and the reaction was conducted at a temperature of 200° C. for 10 hours under vigorously stirring. After cooling, inorganic salts were removed by filtration. The reaction products were analyzed by gas chromatography and by NMR. As the results, it was confirmed that 1,1,3,3-tetrachloro-1,2,2-trifluoropropane (R-223ca), 1,1,1,3-tetrachloro-2,2,3-trifluoropropane (R-223cb), 1,1,3-trichloro-2,2,3,3-tetrafluoropropane (R-224ca), 1,1,3-trichloro-1,2,2,3-tetrafluoropropane (R-224cb), 1,1,1-trichloro-2,2,3,3-tetrafluoropropane (R-224cc), 1,1-dichloro-2,2,3,3,3-pentafluoropropane (R-225ca), 1,3-dichloro-1,1,2,2,3-pentafluoropropane (R-225cb), 1,1-dichloro-1,2,2,3,3-pentafluoropropane (R-225cc), 1 chloro-1,2,2,3,3,3-hexafluoropropane [R-226ca), 1-chloro-1,1,2,2,3,3-hexafluoropropane (R-226cb) and 1,1,1,2,2,3,3-heptafluoropropane (R-227ca), were formed. The results are shown in Table 12-1.

TABLE 12-1

| Conversion of R-222ca | 99% |
|---|---|
| Selectivity for R-224ca | 6% |
| Selectivity for R-225cb | 25% |
| Selectivity for R-226ca | 13% |
| Selectivity for R-226cb | 7% |
| Selectivity for R-227ca | 2% |

EXAMPLE 12-2

The fluorination reaction and the analysis of the reaction products were conducted in the same manner as in Example 12-1 except that as the starting material, 1,1,3,3-tetrachloro-1,2,2,-trifluoropropane (R-223ca) was used. The results are shown in Table 12-2.

TABLE 12-2

| Conversion of R-223ca | 99% |
|---|---|
| Selectivity for R-224ca | 3% |
| Selectivity for R-225cb | 30% |
| Selectivity for R-226ca | 15% |

TABLE 12-2-continued

| Conversion of R-223ca | 99% |
|---|---|
| Selectivity for R-226cb | 10% |
| Selectivity for R-227ca | 5% |

EXAMPLE 12-3

The fluorination reaction and the analysis of the reaction products were conducted in the same manner as in Example 12-1 except that as the starting material, 1,1,1,3-tetrachloro-2,2,3-trifluoropropane (R-223cb) was used. The results are shown in Table 12-3.

TABLE 12-3

| Conversion of R-223cb | 99% |
|---|---|
| Selectivity for R-225cb | 25% |
| Selectivity for R-226ca | 23% |
| Selectivity for R-226cb | 14% |
| Selectivity for R-227ca | 8% |

EXAMPLE 12-4

The fluorination reaction and the analysis of the reaction products were conducted in the same manner as in Example 12-1 except that as the starting materials, 50 g of 1,1,3-trichloro-2,2,3,3-tetrafluoropropane (R-224ca), 60 g of spray-dried potassium fluoride and 6 g of tetrabutylsulfonium bromide, were used. The results are shown in Table 12-4.

TABLE 12-4

| Conversion of R-224ca | 99% |
|---|---|
| Selectivity for R-225ca | 8% |
| Selectivity for R-225cb | 11% |
| Selectivity for R-226ca | 26% |
| Selectivity for R-226cb | 17% |
| Selectivity for R-227ca | 20% |

EXAMPLE 12-5

The fluorination reaction and the analysis of the reaction products were conducted in the same manner as in Example 12-4 except that as the starting material, 1,1,3-trichloro-1,2,2,3-tetrafluoropropane (R-224cb), was used. The results are shown in Table 12-5.

TABLE 12-5

| Conversion of R-224cb | 99% |
|---|---|
| Selectivity for R-225cb | 14% |
| Selectivity for R-225cc | 12% |
| Selectivity for R-226ca | 21% |
| Selectivity for R-226cb | 22% |
| Selectivity for R-227ca | 21% |

EXAMPLE 12-6

The fluorination reaction and the analysis of the reaction products were conducted in the same manner as in Example 12-4 except that as the starting material, 1,1,1-trichloro-2,2,3,3-tetrafluoropropane (R-224cc), was used. The results are shown in Table 12-6.

TABLE 12-6

| Conversion of R-224cc | 98% |
|---|---|
| Selectivity for R-225cc | 23% |
| Selectivity for R-226cb | 37% |
| Selectivity for R-227ca | 30% |

EXAMPLE 12-7

The fluorination reaction and the analysis of the reaction products were conducted in the same manner as in Example 12-1 except that as the starting materials, 50 g of 1,1-dichloro-2,2,3,3,3-pentafluoropropane (R-225ca), 43 g of spray-dried potassium fluoride and 5 g of tetrabutylsulfonium bromide, were used. The results are shown in Table 12-7.

TABLE 12-7

| Conversion of R-225ca | 94% |
|---|---|
| Selectivity for R-226ca | 44% |
| Selectivity for R-227ca | 42% |

EXAMPLE 12-8

The fluorination reaction and the analysis of the reaction products were conducted in the same manner as in Example 12-7 except that as the starting material, 1,3-dichloro-1,1,2,2,3-pentafluoropropane (R-225cb), was used. The results are shown in Table 12-8.

TABLE 12-8

| Conversion of R-225cb | 93% |
|---|---|
| Selectivity for R-226ca | 22% |
| Selectivity for R-226cb | 21% |
| Selectivity for R-227ca | 39% |

EXAMPLE 12-9

The fluorination reaction and the analysis of the reaction products were conducted in the same manner as in Example 12-7 except that as the starting material, 1,1-dichloro-1,2,2,3,3-pentafluoropropane (R-225cc), was used. The results are shown in Table 12-9.

TABLE 12-9

| Conversion of R-225cc | 96% |
|---|---|
| Selectivity for R-226cb | 34% |
| Selectivity for R-227ca | 47% |

EXAMPLE 12-10

The fluorination reaction and the analysis of the reaction products were conducted in the same manner as in Example 12-1 except that as the starting materials, 50 g of 1-chloro-1,2,2,3,3,3-hexafluoropropane (R-226ca), 25 g of spary-dried potassium fluoride and 3 g of tetrabutylsulfonium bromide, were used. The results are shown in Table 12-10

TABLE 12-10

| Conversion of R-226ca | 89% |
|---|---|
| Selectivity for R-227ca | 79% |

EXAMPLE 12-11

The fluorination reaction-and the analysis of the reaction products were conducted in the same manner as in Example 12-1 except that as the starting materials, 50 g of 1-chloro-1,1,2,2,3,3-hexafluoropropane (R-226cb), 65 g of cesium fluoride and 7 g of tetrabutylammonium bromide, were used. The results are shown in Table 12-11.

TABLE 12-11

| Conversion of R-226cb | 85% |
|---|---|
| Selectivity for R-227ca | 80% |

EXAMPLE 12-12

Into a 200 ml Hastelloy C autoclave, as the starting materials, 150 g of 1,1,1-trichloro-2,2,3,3-tetrafluoropropane (R-224cc) and 60 g of antimony trifluoride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 12-12.

TABLE 12-12

| Conversion of R-224cc | 20% |
|---|---|
| Selectivity for R-225cc | 72% |
| Selectivity for R-226cb | 18% |
| Selectivity for R-227ca | 6% |

EXAMPLE 12-13

Into a 200 ml Hastelloy C autoclave, as the starting materials, 150 g of 1,1,1-trichloro-2,2,3,3-tetrafluoropropane (R-224cc), 60 g of antimony trifluoride and 3 g of antimony trichloride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 12-13.

TABLE 12-13

| Conversion of R-224cc | 29% |
|---|---|
| Selectivity for R-225cc | 63% |
| Selectivity for R-226cb | 28% |
| Selectivity for R-227ca | 5% |

EXAMPLE 12-14

Into a 200 ml Hastelloy C autoclave, as the starting materials, 150 g of 1,1,1-trichloro-2,2,3,3-tetrafluoropropane (R-224cc), 60 g of antimony trifluoride and 3 g of antimony pentachloride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 12-14.

TABLE 12-14

| Conversion of R-224cc | 31% |
|---|---|
| Selectivity for R-225cc | 64% |
| Selectivity for R-226cb | 25% |
| Selectivity for R-227ca | 6% |

EXAMPLE 12-15

Into a 200 ml Hastelloy C autoclave, 60 g of antimony trifluoride was added, and then 23 g of chlorine gas was introduced to prepare antimony dichloride trifluoride. The thin film of antimony dichloride trifluoride thereby formed was broken. Then, as the starting material, 150 g of 1,1,1-trichloro-2,2,3,3-tetrafluoropropane (R-224cc) was charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 12-15.

TABLE 12-15

| Conversion of R-224cc | 35% |
|---|---|
| Selectivity for R-225cc | 63% |
| Selectivity for R-226cb | 26% |
| Selectivity for R-227ca | 5% |

EXAMPLE 12-16

Into a 200 ml Hastelloy C autoclave, as the starting materials, 150 g of 1,1,1-trichloro-2,2,3,3-tetrafluoropropane (R-224cc) and 80 g of antimony pentafluoride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 12-16.

TABLE 12-16

| Conversion of R-224cc | 36% |
|---|---|
| Selectivity for R-225cc | 68% |
| Selectivity for R-226cb | 22% |
| Selectivity for R-227ca | 7% |

EXAMPLE 13-1

Into a 1 l Hastelloy C autoclave, as the starting material, 50 g of 1,1,1,3-tetrachloro-2,2-difluoropropane (R-232cb), 80 g of spray-dried potassium fluoride, 8 g of tetrabutylsulfonium bromide and 480 g of sulfolane, were charged, and the reaction was conducted at a temperature of 200° C. for 10 hours under vigorously stirring. After cooling, inorganic salts were removed by filtration, and the reaction products were analyzed by gas chromatography and by NMR. As the results, it was confirmed that 1,1,1-trichloro-2,2,3-trifluoorpropane (R-233cc), 1,1-dichloro-1,2,2,3-tetrafluoropropane (R-234cd), 1,3-dichloro-1,1,2,2-tetrafluoropropane (R-244cc), 1-chloro-1,1,2,2,3-pentafluoropropane (R-235cc) and 1,1,1,2,2,3-hexafluoropropane (R-236cb), were formed. The results are shown in Table 13-1.

TABLE 13-1

| Conversion of R-232cb | 99% |
|---|---|
| Selectivity for R-233cc | 10% |
| Selectivity for R-234cc | 27% |
| Selectivity for R-234cd | 13% |
| Selectivity for R-235cc | 14% |
| Selectivity for R-236cb | 10% |

EXAMPLE 13-2

The fluorination reaction and the analysis of the reaction products were conducted in the same manner as in Example 13-1 except that as the starting material, 1,1,3,3-tetrachloro-2,2-difluoropropane (R-232ca) was used. The results are shown in Table 13-2.

TABLE 13-2

| Conversion of R-232ca | 99% |
|---|---|
| Selectivity for R-234ca | 15% |
| Selectivity for R-234cb | 12% |
| Selectivity for R-235ca | 35% |
| Selectivity for R-236ca | 10% |

EXAMPLE 13-3

The fluorination reaction and the analysis of the reaction products were conducted in the same manner as in Example 13-1 except that as the starting materials, 50 g of 1,1,1-trichloro-2,2,3-trifluoropropane (R-233cc), 65 g of spray-dried potassium fluoride and 6.5 g of tetrabutylsulfonium bromide, were used. The results are shown in Table 13-3.

TABLE 13-3

| Conversion of R-233cc | 99% |
|---|---|
| Selectivity for R-234cd | 17% |
| Selectivity for R-235cc | 30% |
| Selectivity for R-236cb | 38% |

EXAMPLE 13-4

The fluorination reaction and the analysis of the reaction products were conducted in the same manner as in Example 13-3 except that as the starting material, 1,1,1-trichloro-1,2,2-trifluoropropane (R-233cb), was used. The results are shown in Table 13-4.

TABLE 13-4

| Conversion of R-233cb | 99% |
|---|---|
| Selectivity for R-234cc | 13% |
| Selectivity for R-234cd | 11% |
| Selectivity for R-235cb | 23% |
| Selectivity for R-235cc | 15% |
| Selectivity for R-236cb | 20% |

EXAMPLE 13-5

The fluorination reaction and the analysis of the reaction products were conducted in the same manner as in Example 13-3 except that as the starting material, 1,1,3-trichloro-2,2,3-trifluoropropane (R-233cb), was used. The results are shown in Table 13-5.

TABLE 13-5

| Conversion of R-233ca | 99% |
|---|---|
| Selectivity for R-234ca | 11% |
| Selectivity for R-234cb | 11% |
| Selectivity for R-235ca | 35% |
| Selectivity for R-236ca | 25% |

EXAMPLE 13-6

The fluorination reaction and the analysis of the reaction products were conducted in the same manner as in Example 13-1 except that as the starting materials, 50 g of 1,1-dichloro-1,2,2,3-tetrafluoropropane (R-234cd), 50 g of spray-dried potassium fluoride and 5 g of tetrabutylsulfonium bromide, were used. The results are shown in Table 13-6.

TABLE 13-6

| Conversion of R-234cd | 93% |
|---|---|
| Selectivity for R-235cc | 27% |
| Selectivity for R-236cb | 59% |

EXAMPLE 13-7

The fluorination reaction and the analysis of the reaction products were conducted in the same manner as in Example 13-6 except that as the starting material, 1,3-dichloro-1,1,2,2-tetrafluoropropane (R-234cc), as used. The results are shown in Table 13-7.

TABLE 13-7

| Conversion of R-234cc | 94% |
|---|---|
| Selectivity for R-235cb | 31% |
| Selectivity for R-235cc | 21% |
| Selectivity for R-236cb | 30% |

EXAMPLE 13-8

The fluorination reaction and the analysis of the reaction products were conducted in the same manner as in Example 13-6 except that as the starting material, 1,1-dichloro-2,2,3,3-tetrafluoropropane (R-234cb), was used. The results are shown in Table 13-8.

TABLE 13-8

| Conversion of R-234cb | 91% |
|---|---|
| Selectivity for R-235ca | 27% |
| Selectivity for R-236ca | 51% |

EXAMPLE 13-9

The fluorination reaction and the analysis of the reaction products were conducted in the same manner as in Example 13-6 except that as the starting material, 1,3-dichloro-1,2,2,3-tetrafluoropropane (R-234ca), was used. The results are shown in Table 13-9.

TABLE 13-9

| Conversion of R-234ca | 94% |
|---|---|
| Selectivity for R-235ca | 31% |
| Selectivity for R-236ca | 52% |

EXAMPLE 13-10

The fluorination reaction and the analysis of the reaction products were conducted in the same manner as in Example 13-1 except that as the starting materials, 50 g of 1-chloro-1,1,2,2,3-pentafluoropropane (R-235cc), 30 g of spray-dried potassium fluoride and 3 g of tetrabutylsulfonium bromide, were used. The results are shown in Table 13-10.

TABLE 13-10

| Conversion of R-235cc | 88% |
|---|---|
| Selectivity for R-236cb | 80% |

EXAMPLE 13-11

The fluorination reaction and the analysis of the reaction products were conducted in the same manner as in Example 13-10 except that as the starting material, 3-chloro-1,1,1,2,2-pentafluoropropane (R-235cb), was used. The results are shown in Table 13-11.

TABLE 13-11

| Conversion of R-235cb | 85% |
|---|---|
| Selectivity for R-236cb | 76% |

EXAMPLE 13-12

The fluorination reaction and the analysis of the reaction products were conducted in the same manner as in Example 13-1 except that as the starting material, 50 g of 1-chloro-1,2,2,3,3-pentafluoropropane (R-235ca), 78 g of cesium fluoride and 8 g of tetrabutylammonium bromide, were used and the reaction temperature was changed to 150° C. The results are shown in Table 13-12.

TABLE 13-12

| Conversion of R-235ca | 89% |
|---|---|
| Selectivity for R-236ca | 80% |

EXAMPLE 13-13

Into a 200 ml Hastelloy C autoclave, as the starting materials, 150 g of 1,1,1-trichloro-2,2,3-trifluoropropane (R-233cc) and 70 g of antimony trifluoride, were changed, and the reaction was conducted at a temperature of 150° C. for 10 hours under vigorously stirring. After cooling, inorganic salts were removed by filtration, and the crude reaction solution was washed with water and dried. Them, the reaction products were analyzed by gas chromatography and by NMR. The results are shown in Table 13-13.

TABLE 13-13

| Conversion of R-233cc | 25% |
|---|---|
| Selectivity for R-234cd | 69% |
| Selectivity for R-235cc | 18% |
| Selectivity for R-236cb | 9% |

EXAMPLE 13-14

Into a 200 ml Hastelloy C autoclave, as the starting materials, 150 g of 1,1,1-trichloro-2,2,3-trifluoropropane (R-233cc), 70 g of antimony trifluoride and 3 g of antimony trichloride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 13-14.

TABLE 13-14

| Conversion of R-233cc | 32% |
|---|---|
| Selectivity for R-234cd | 64% |
| Selectivity for R-235cc | 28% |
| Selectivity for R-236cb | 6% |

EXAMPLE 13-15

Into a 200 ml Hastelloy C autoclave, as the starting material, 150 g of 1,1,1-trichloro-2,2,3-trifluoropropane (R-233cc), 70 g of antimony trifluoride and 3 g of antimony pentachloride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 13-15.

TABLE 13-15

| Conversion of R-233cc | 33% |
|---|---|
| Selectivity for R-234cd | 66% |
| Selectivity for R-235cc | 22% |
| Selectivity for R-236cb | 8% |

EXAMPLE 13-16

Into a 200 ml Hastelloy C autoclave, 70 g of antimony trifluoride was added, and then 25 g of chlorine gas was introduced to prepare antimony dichloride trifluoride. The thin film of antimony dichloride trifluoride thereby formed was broken, and then as the starting material, 150 g of 1,1,1-trichloro-2,2,3-trifluoropropane (R-233cc) was charged. The reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 13-16.

TABLE 13-16

| Conversion of R-233cc | 36% |
|---|---|
| Selectivity for R-234cd | 66% |
| Selectivity for R-235cc | 24% |
| Selectivity for R-236cb | 8% |

EXAMPLE 13-17

Into a 200 ml Hastelloy C autoclave, as the starting materials, 150 g of 1,1,1-trichloro-2,2,3-trifluoropropane (R-233cc) and 100 g of antimony pentafluoride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 13-17.

TABLE 13-17

| Conversion of R-233cc | 39% |
|---|---|
| Selectivity for R-234cd | 67% |
| Selectivity for R-235cc | 24% |
| Selectivity for R-236cb | 7% |

EXAMPLE 14-1

Into a 1 l Hastelloy C autoclave, as the starting materials, 50 g of 1,1,3-trichloro-2,2-difluoropropane (R-242ca), 70 g of spray-dried potassium fluoride, 7 g of tetrabutylphosphonium bromide and 480 g of sulfolane, were charged, and the reaction was conducted at a temperature of 200° C. for 10 hours under vigorously stirring. After cooling, inorganic salts were removed by filtration, and the reaction products were analyzed by gas chromatography and by NMR. As the results, it was confirmed that 1,3-dichloro-1,2,2-trifluoropropane (R-243ca), 1,1-dichloro-2,2,3-trifluoropropane (R-243cb), 1-chloro-2,2,3,3-tetrafluoropropane (R-244ca), 1-chloro-1,2,2,3-tetrafluoropropane (R-244cb) and 1,1,2,2,3-pentafluoropropane (R-245ca), were formed. The results are shown in Table 14-1.

TABLE 14-1

| Conversion of R-242ca | 99% |
|---|---|
| Selectivity for R-243ca | 11% |
| Selectivity for R-243cb | 10% |
| Selectivity for R-244ca | 21% |
| Selectivity for R-244cb | 24% |
| Selectivity for R-245ca | 9% |

EXAMPLE 14-2

The fluorination reaction and the analysis of the reaction products were conducted in the same manner as in Example 14-1 except that as the starting material, 1,1,1-trichloro-2,2-difluoropropane (R-242cb) was used. The results are shown in Table 14-2.

TABLE 14-2

| Conversion of R-242cb | 99% |
|---|---|
| Selectivity for R-243cc | 8% |
| Selectivity for R-244cc | 39% |
| Selectivity for R-245cb | 34% |

EXAMPLE 14-3

The fluorination reaction and the analysis of the reaction products were conducted in the same manner as in Example 14-1 except that as the starting materials, 50 g of 1,3-dichloro-1,2,2-trifluoropropane (R-243ca), 50 g of spray-dried potassium fluoride and 5 g of tetrabutylsulfonium bromide, were used. The results are shown in Table 14-3.

TABLE 14-3

| Conversion of R-243ca | 94% |
|---|---|
| Selectivity for R-244ca | 22% |
| Selectivity for R-244cb | 19% |
| Selectivity for R-245ca | 36% |

EXAMPLE 14-4

The fluorination reaction and the analysis of the reaction products were conducted in the same manner as in Example 14-3 except that as the starting material, 1,1-dichloro-2,2,3-trifluoropropane (R-243cb) was used. The results are shown in Table 14-4.

TABLE 14-4

| Conversion of R-243cb | 95% |
|---|---|
| Selectivity for R-244cb | 34% |
| Selectivity for R-245ca | 51% |

EXAMPLE 14-5

The fluorination reaction and the analysis of the reaction products were conducted in the same manner as in Example 14-3 except that as the starting material, 1,1-dichloro-1,2,2-trifluoropropane (R-243cc) was used. The results are shown in Table 14-5.

TABLE 14-5

| Conversion of R-243cc | 96% |
|---|---|
| Selectivity for R-244cc | 18% |
| Selectivity for R-245cc | 70% |

EXAMPLE 14-6

The fluorination reaction and the analysis of the reaction products were conducted in the same manner as in Example 14-1 except that as the starting materials, 50 g of 1-chloro-2,2,3,3-tetrafluoropropane (R-244ca), 30 g of spray-dried potassium fluoride and 3 g of tetrabutylphosphonium bromide, were used. The results are shown in Table 14-6.

TABLE 14-6

| | |
|---|---|
| Conversion of R-244ca | 88% |
| Selectivity for R-245ca | 89% |

EXAMPLE 14-7

The fluorination reaction and the analysis of the reaction products were conducted in the same manner as in Example 14-6 except that as the starting material, 1-chloro-1,2,2,3-tetrafluoropropane (R-244cb), was used. The results are shown in Table 14-7.

TABLE 14-7

| | |
|---|---|
| Conversion of R-244cb | 89% |
| Selectivity for R-245ca | 84% |

EXAMPLE 14-8

The fluorination reaction and the analysis of the reaction products were conducted in the same manner as in Example 14-1 except that as the starting materials, 50 g of 1-chloro-1,1,2,2-tetrafluoropropane (R-244cc), 78 g of cesium fluoride and 8 g of tetrabutylammonium bromide, were used and the reaction temperature was changed to 150° C. The results are shown in Table 14-8.

TABLE 14-8

| | |
|---|---|
| Conversion of R-244cb | 87% |
| Selectivity for R-245cc | 82% |

EXAMPLE 14-9

Into a 200 ml Hastelloy C autoclave, as the starting materials, 150 g of 1,1-dichloro-1,2,2-trifluoropropane (R-243cc) and 80 g of antimony trifluoride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 14-9. Table

TABLE 14-9

| | |
|---|---|
| Conversion of R-243cc | 30% |
| Selectivity for R-244cc | 75% |
| Selectivity for R-245cb | 22% |

EXAMPLE 14-10

Into a 200 ml Hastelloy C autoclave, as the starting material, 150 g of 1,1-dichloro-1,2,2-trifluoropropane (R-243cc), 80 g of antimony trifluoride and 3 g of antimony trichloride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 14-10.

TABLE 14-10

| | |
|---|---|
| Conversion of R-243cc | 36% |
| Selectivity for R-244cc | 70% |
| Selectivity for R-245cb | 28% |

EXAMPLE 14-11

Into a 200 ml Hastelloy C autoclave, as the starting materials, 150 g of 1,1-dichloro-1,2,2-trifluoropropane (R-243cc), 80 g of antimony trifluoride and 3 g of antimony pentachloride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 14-11.

TABLE 14-11

| | |
|---|---|
| Conversion of R-243cc | 37% |
| Selectivity for R-244cc | 69% |
| Selectivity for R-245cb | 29% |

EXAMPLE 14-12

Into a 200 ml Hastelloy C autoclave, 80 g of antimony trifluoride was added, and then 30 g of chlorine gas was introduced to prepare antimony dichloride trifluoride. The thin film of antimony dichloride trifluoride thereby formed was broken, and then as the starting material, 150 g of 1,1--dichloro-1,2,2-trifluoropropane (R-243cc), was charged. The reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 14-12.

TABLE 14-12

| | |
|---|---|
| Conversion of R-243cc | 39% |
| Selectivity for R-244cc | 75% |
| Selectivity for R-245cb | 24% |

EXAMPLE 14-13

Into a 200 ml Hastelloy C autoclave, as the starting materials, 150 g of 1,1-dichloro-1,2,2-trifluoropropane (R-243cc) and 110 g of antimony pentafluoride, were charged, and the reaction was conducted at a temperature of 150° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 14-13.

TABLE 14-13

| | |
|---|---|
| Conversion of R-243cc | 41% |
| Selectivity for R-244cc | 72% |

TABLE 14-13-continued

| Conversion of R-243cc | 41% |
|---|---|
| Selectivity for R-245cb | 26% |

EXAMPLE 15-1

Into a 1 l Hastelloy C autoclave, as the starting materials, 50 g of 1,3-dichloro-2,2-difluoropropane (R-252ca), 60 g of spray-dried potassium fluoride, 6 g of tetrabutylphosphonium bromide and 480 g of sulfolane, were charged, and the reaction was conducted at a temperature of 200° C. for 10 hours under vigorously stirring. After cooling, inorganic salts were removed by filtration, and the reaction products were analyzed by gas chromatography and by NMR. As the results, it was confirmed that 1-chloro-2,2,3-trifluoropropane (R-253ca) and 1,2,2,3-tetrafluoropropane (R-254ca), were formed. The results are shown in Table 15-1.

TABLE 15-1

| Conversion of R-251ca | 89% |
|---|---|
| Selectivity for R-253ca | 31% |
| Selectivity for R-254ca | 55% |

EXAMPLE 15-2

The fluorination reaction and the analysis of the reaction products were conducted in the same manner as in Example 15-1 except that as the starting material, 1,1-dichloro-2,2-difluoropropane (R-252cb) was used. The results are shown in Table 15-2.

TABLE 15-2

| Conversion of R-252ca | 91% |
|---|---|
| Selectivity for R-253ca | 31% |
| Selectivity for R-254ca | 55% |

EXAMPLE 15-3

The fluorination reaction and the analysis of the reaction products were conducted in the same manner as in Example 15-1 except that as the starting materials, 50 g of 1-chloro-2,2,3-trifluoropropane (R-253ca), 33 g of spray-dried potassium fluoride and 4 g of tetrabutyl-phosphonium bromide, were used. The results are shown in Table 15-3.

TABLE 15-3

| Conversion of R-253ca | 79% |
|---|---|
| Selectivity for R-254ca | 70% |

EXAMPLE 15-4

The fluorination reaction and the analysis of the reaction products were conducted in the same manner as in Example 15-1 except that as the starting materials, 50 g of 1-chloro-1,2,2-trifluoropropane (R-253cb), 86 g of cesium fluoride and 9 g of tetrabutylammonium bromide, were used and the reaction temperature was changed to 150° C. The results are shown in Table 15-4.

TABLE 15-4

| Conversion of R-253ca | 82% |
|---|---|
| Selectivity for R-254ca | 75% |

EXAMPLE 15-5

Into a 200 ml Hastelloy C autoclave, as the starting materials, 150 g of 1-chloro-1,2,2-trifluoropropane (R-253cb) and 100 g of antimony trifluoride, were charged, and the reaction was conducted at a temperature of 200° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 15-5.

TABLE 15-5

| Conversion of R-253cb | 3% |
|---|---|
| Selectivity for R-254cb | 95% |

EXAMPLE 15-6

Into a 200 ml Hastelloy C autoclave, as the starting materials, 150 g of 1-chloro-1,2,2-trifluoropropane (R-253cb), 100 g of antimony trifluoride and 3 g of antimony trichloride, were charged, and the reaction was conducted at a temperature of 200° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 15-6.

TABLE 15-6

| Conversion of R-253cb | 4% |
|---|---|
| Selectivity for R-254cb | 98% |

EXAMPLE 15-7

Into a 200 ml Hastelloy C autoclave, as the starting materials, 150 g of 1-chloro-1,2,2-trifluoropropane (R-253cb), 100 g of antimony trifluoride and 3 g of antimony pentachloride, were charged, and the reaction was conducted at a temperature of 200° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 15-7.

TABLE 15-7

| Conversion of R-253cb | 6% |
|---|---|
| Selectivity for R-254cb | 97% |

EXAMPLE 15-8

Into a 200 ml Hastelloy C autoclave, 100 g of antimony trifluoride was added, and then 40 g of chlorine gas was introduced to prepare antimony dichloride trifluoride. The thin film of antimony dichloride trichloride thereby formed was broken, and then as the starting material, 150 g of 1-chloro-1,2,2-trifluoropropane (R-253cb) was charged. The reaction was conducted at a temperature of 200° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 15-8.

TABLE 15-8

| Conversion of R-253cb | 10% |
|---|---|
| Selectivity for R-254cb | 98% |

EXAMPLE 15-9

Into a 200 ml Hastelloy C autoclave, as the starting materials, 150 g of 1-chloro-1,2,2-trifluoropropane (R-253cb) and 110 g of antimony pentafluoride, were charged, and the reaction was conducted at a temperature of 200° C. for 10 hours under vigorously stirring. After cooling, inorganic salts were removed by filtration, and the crude reaction solution was washed with water and dried. Then, the reaction products were analyzed by gas chromatography and by NMR. The results are shown in Table 15-9.

TABLE 15-9

| Conversion of R-253cb | 11% |
|---|---|
| Selectivity for R-254cb | 96% |

The present invention is effective for the preparation of 2,2-difluoropropanes selectively by reacting chlorine-containing 2,2-halogenopropanes with hydrogen fluoride or a fluorinating agent.

We claim:

1. A process for producing a 2,2-difluoropropane of the following formula (2), which comprises fluorinating a chlorine-containing 2,2-difluoropropane of the following formula (1) with hydrogen fluoride in a gas phase, in the presence of a fluorination catalyst comprising (A) a halide or oxide at least one element selected from the group consisting of Al and Cr, and
(B) a halide or oxide at least one element selected from the group consisting of Mg, Ca, Ba, Sr, Fe, Ni, Co, and Mn, said fluorination being conducted at a reaction temperature of from 150° C.–550° C.

(1) $C_3H_aCl_bF_c$
(2) $C_3H_aCL_{b-x}F_{c+x}$ wherein a, b, c and x are integers satisfying the following conditions:
$a \geq 0$, $b \geq 1$, $c \geq 2$, $x \geq 1$,
$a+b+c=8$.

2. The process according to claim 1, wherein the chlorine-containing 2,2-difluoropropane of the formula (1) is $C_3HCl_{5-m^2}F_{2+m^2}$ ($0 \leq m^2 \leq 4$), and the 2,2-difluoropropane of the formula (2) is $C_3HCl_{5-n^2}F_{2+n^2}$ ($1 \leq n^2 \leq 5$, $m^2 < n^2$).

3. The process according to claim 1, wherein the chlorine-containing 2,2-difluoropropane of the formula (1) is $C_3H_2Cl_{4-m^3}F_{2+m^3}$ ($0 \leq m^3 \leq 3$), and the 2,2-difluoropropane of the formula (2) is $C_3H_2Cl_{4-n^3}F_{2+n^3}$ ($1 \leq n^3 \leq 4$, $m^3 < n^3$).

4. The process according to claim 1, wherein the chlorine-containing 2,2-difluoropropane of the formula (1) is $C_3H_3Cl_{3-m^4}F_{2+m^4}$ ($0 \leq m^4 \leq 2$), and the 2,2-difluoropropane of the formula (2) is $C_3H_3Cl_{3-n^4}F_{2+n^4}$ ($1 \leq n^4 \leq 3$, $m^4 < n^4$).

5. The process according to claim 1, wherein the chlorine-containing 2,2-halogenopropane of the formula (1) is $C_3H_4Cl_{2-m^5}F_{2+m^5}$ ($0 \leq m^5 \leq 1$), and the 2,2-difluoropropane of the formula (2) is $C_3H_4Cl_{2-n^5}F_{2+n^5}$ ($1 \leq n^5 \leq 2$, $m^5 < n^5$).

6. The process according to claim 1, wherein the chlorine-containing 2,2-difluoropropane of the formula (1) is $C_3Cl_{6-m^1}F_{2+m^1}$ ($0 \leq m^1 \leq 5$), and the 2,2-difluoropropane of the formula (2) is $C_3Cl_{6-n^1}F_{2+n^1}$ ($1 \leq n^1 \leq b$, $m^1 < n^1$).

* * * * *

UNITED STATES PATENT AND TRADEMARK OFFICE
CERTIFICATE OF CORRECTION

PATENT NO. : 5,264,639
DATED : November 23, 1993
INVENTOR(S) : Shinsuke Morikawa et al.

It is certified that error appears in the above-indentified patent and that said Letters Patent is hereby corrected as shown below:

On the title page, Item [63],

The Related U.S. Application Data, should read:

--Continuation of Ser. No. 582,197, Oct. 2, 1990, filed as

PCT/JP90/00123, Feb. 1, 1990, abandoned--

Signed and Sealed this

Thirtieth Day of August, 1994

Attest:

BRUCE LEHMAN

*Attesting Officer*      *Commissioner of Patents and Trademarks*